United States Patent
Shluzas

(10) Patent No.: US 7,144,396 B2
(45) Date of Patent: Dec. 5, 2006

(54) APPARATUS FOR CONNECTING A LONGITUDINAL MEMBER TO A BONE PORTION

(75) Inventor: Alan E. Shluzas, Millis, MA (US)

(73) Assignee: Endius Incorporated, Plainville, MA (US)

( * ) Notice: Subject to any disclaimer, the term of this patent is extended or adjusted under 35 U.S.C. 154(b) by 0 days.

(21) Appl. No.: 10/483,605

(22) PCT Filed: Feb. 13, 2003

(86) PCT No.: PCT/US03/04361

§ 371 (c)(1),
(2), (4) Date: Jan. 13, 2004

(87) PCT Pub. No.: WO03/068083

PCT Pub. Date: Aug. 21, 2003

(65) Prior Publication Data

US 2004/0176766 A1    Sep. 9, 2004

Related U.S. Application Data

(63) Continuation-in-part of application No. 10/075,668, filed on Feb. 13, 2002, and a continuation-in-part of application No. 10/087,489, filed on Mar. 1, 2002.

(51) Int. Cl.
*A61B 17/56* (2006.01)
*A61F 2/30* (2006.01)

(52) U.S. Cl. .................................................. 606/61

(58) Field of Classification Search .............. 606/60, 606/61, 72, 73
See application file for complete search history.

(56) References Cited

U.S. PATENT DOCUMENTS 5,005,562 A    4/1991    Cotrel
(Continued)

FOREIGN PATENT DOCUMENTS

WO    WO 03/068083    8/2003

OTHER PUBLICATIONS

*Amendment after Final* for U.S. Appl. No. 10/075,668, filed Feb. 13, 2002 (Publication No. 2003/013911 A1)(A31-6014(ENDIUS.061A)) in 11 pages.

(Continued)

*Primary Examiner*—Eduardo C. Robert
*Assistant Examiner*—Anu Ramana
(74) *Attorney, Agent, or Firm*—Knobbe Martens Olson & Bear LLP

(57) ABSTRACT

An apparatus (10) includes a fastener (16) engageable with a bone portion to connect a longitudinal member (12) to the bone portion. A housing (40) has a first passage (42) configured to receive the longitudinal member and a second passage (44) extending transverse to the first passage. The fastener extends through an opening (50) in the housing into the second passage. A longitudinal axis (18) of the fastener is positionable in any one of a plurality of angular positions relative to a longitudinal axis (46) of the second passage. A spacer (60) received in the second passage of the housing is engageable with the fastener and the longitudinal member. A positioning member (70) applies a force to prevent relative movement between the fastener and the housing and permit manual movement of the fastener relative to the housing against the force when the longitudinal member is disengaged from the spacer. A clamping mechanism (90) clamps the longitudinal member, the spacer, and the housing to the fastener to prevent movement of the fastener relative to the housing.

36 Claims, 12 Drawing Sheets

U.S. PATENT DOCUMENTS

| | | | |
|---|---|---|---|
| 5,135,489 A | 8/1992 | Jepson et al. | |
| 5,207,678 A | 5/1993 | Harms et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,613,968 A | 3/1997 | Lin | |
| 5,639,074 A * | 6/1997 | Greenhill et al. | 267/162 |
| 5,669,911 A | 9/1997 | Errico et al. | |
| 5,672,176 A | 9/1997 | Biedermann et al. | |
| 5,690,630 A | 11/1997 | Errico et al. | |
| 5,733,285 A | 3/1998 | Errico et al. | |
| 5,797,911 A | 8/1998 | Sherman et al. | |
| 5,817,094 A | 10/1998 | Errico et al. | |
| 5,876,402 A | 3/1999 | Errico et al. | |
| 5,879,350 A | 3/1999 | Sherman et al. | |
| 5,885,286 A | 3/1999 | Sherman et al. | |
| 6,010,503 A | 1/2000 | Richelsoph et al. | |
| 6,022,350 A | 2/2000 | Ganem | |
| 6,063,090 A * | 5/2000 | Schlapfer | 606/61 |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen et al. | |
| 6,090,111 A | 7/2000 | Nichols | |
| 6,113,601 A | 9/2000 | Tatar | |
| 6,139,550 A | 10/2000 | Michelson | |
| 6,261,287 B1 | 7/2001 | Metz-Stavenhagen et al. | |
| 6,280,442 B1 | 8/2001 | Barker et al. | |
| 6,287,311 B1 | 9/2001 | Sherman et al. | |
| 6,296,642 B1 | 10/2001 | Morrison et al. | |
| 6,302,888 B1 | 10/2001 | Mellinger et al. | |
| 6,375,657 B1 | 4/2002 | Doubler et al. | |
| 6,402,752 B1 | 6/2002 | Schaffler-Wachter et al. | |
| 6,440,137 B1 | 8/2002 | Horvath et al. | |
| 6,454,768 B1 | 9/2002 | Jackson | |
| 6,485,491 B1 | 11/2002 | Farris et al. | |
| 6,488,681 B1 | 12/2002 | Martin et al. | |
| 6,511,099 B1 | 1/2003 | Bartholoma et al. | |
| 6,530,929 B1 | 3/2003 | Justis et al. | |
| 6,537,276 B1 | 3/2003 | Metz-Stavenhagen et al. | |
| 6,540,748 B1 | 4/2003 | Lombardo | |
| 6,547,725 B1 * | 4/2003 | Paolitto et al. | 600/201 |
| 6,551,323 B1 | 4/2003 | Doubler et al. | |
| 6,565,567 B1 | 5/2003 | Haider | |
| 6,585,740 B1 | 7/2003 | Schlapfer et al. | |
| 6,726,687 B1 | 4/2004 | Jackson | |
| 6,835,196 B1 | 12/2004 | Biedermann et al. | |
| 6,837,889 B1 | 1/2005 | Shluzas | |
| 2001/0001119 A1 | 5/2001 | Lombardo | |
| 2002/0091386 A1 | 7/2002 | Martin et al. | |
| 2002/0138076 A1 | 9/2002 | Biedermann et al. | |
| 2003/0004512 A1 | 1/2003 | Farris et al. | |
| 2003/0153911 A1 | 8/2003 | Shluzas | |
| 2004/0153088 A1 | 8/2004 | Janowski et al. | |

OTHER PUBLICATIONS

*Supplemental Notice of Allowability* including Examiner's Amendment for U.S. Appl. No. 10/075,668, filed Feb. 13, 2002 (Publication No. 2003/013911 A1)(A31-6014(ENDIUS.061A)) in 10 pages.

\* cited by examiner

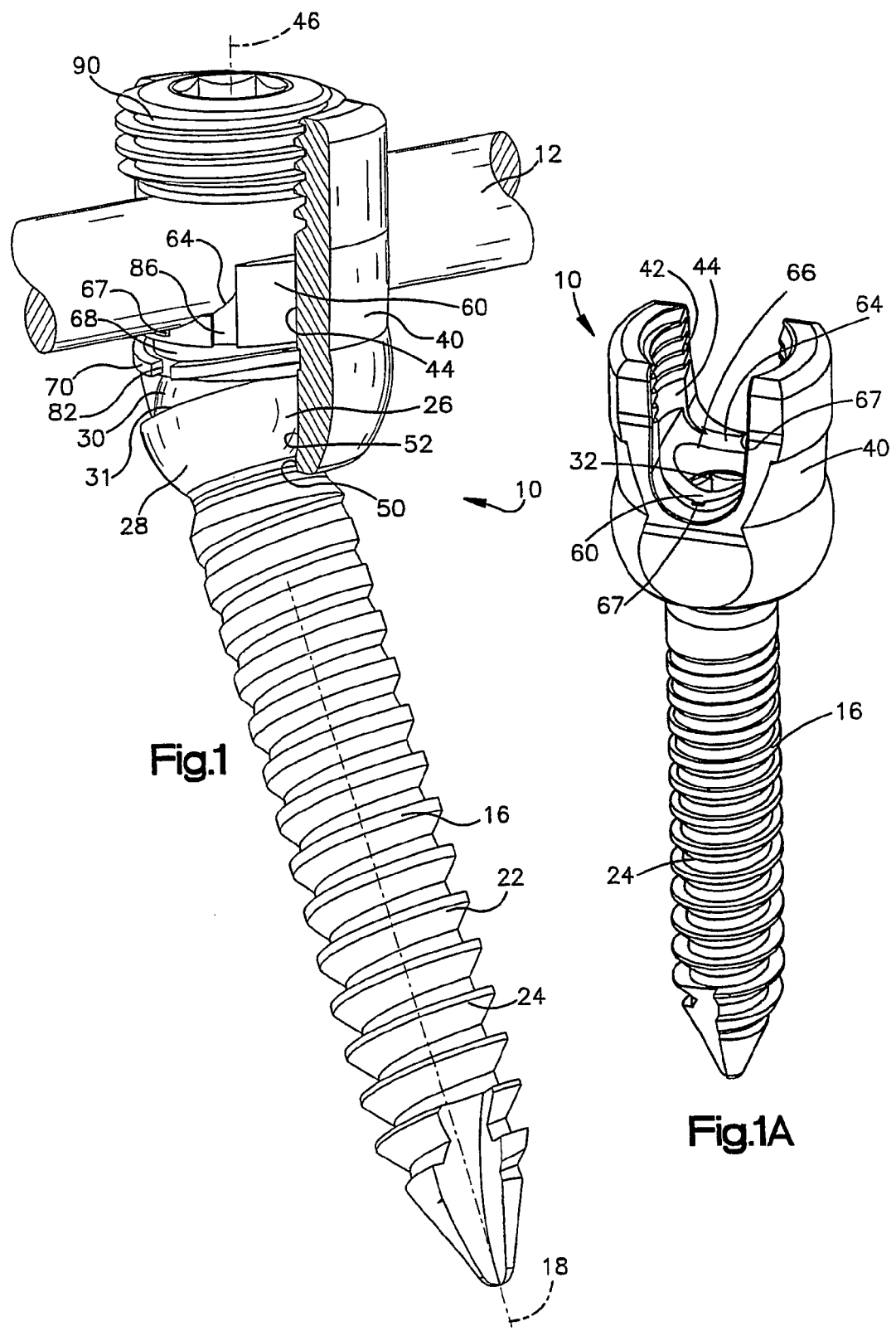

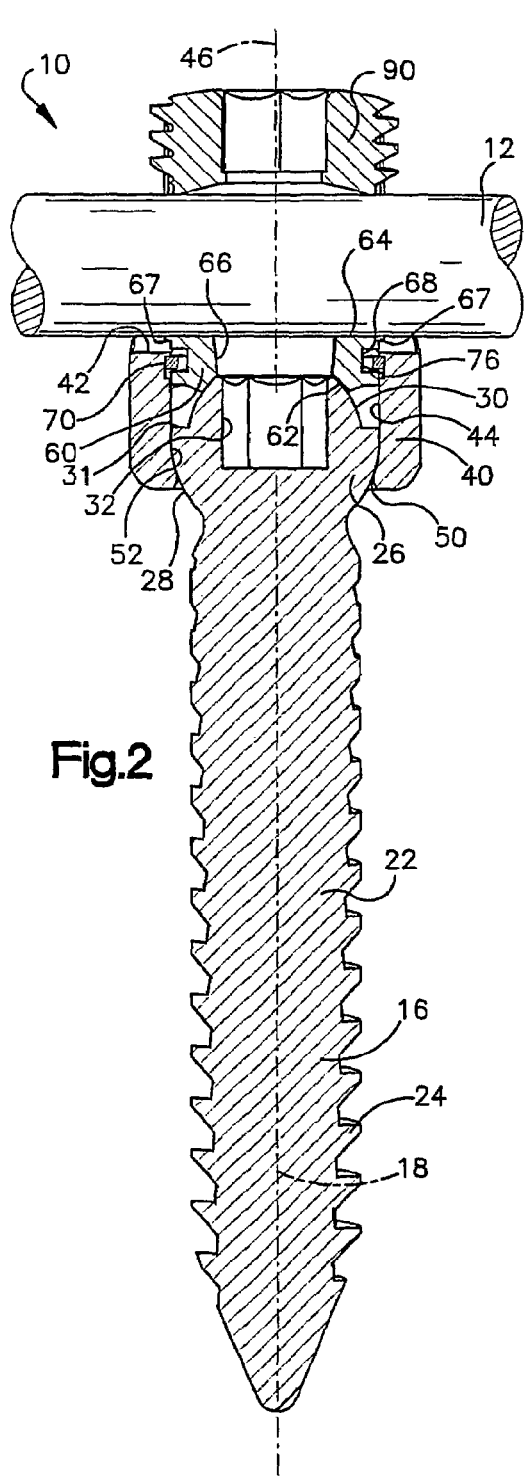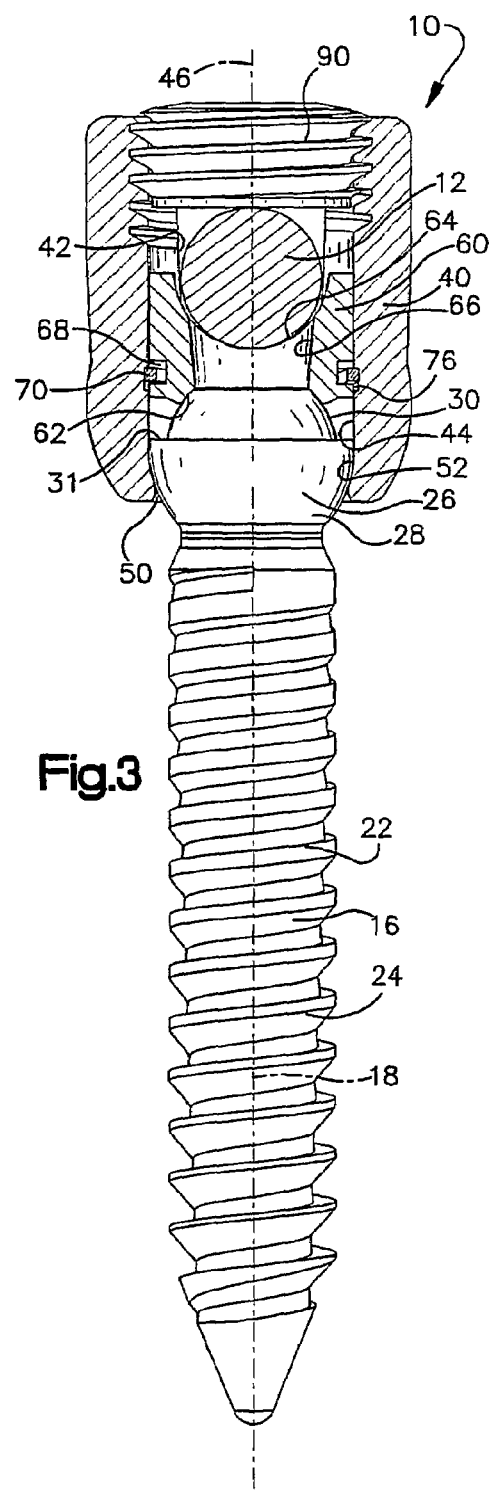

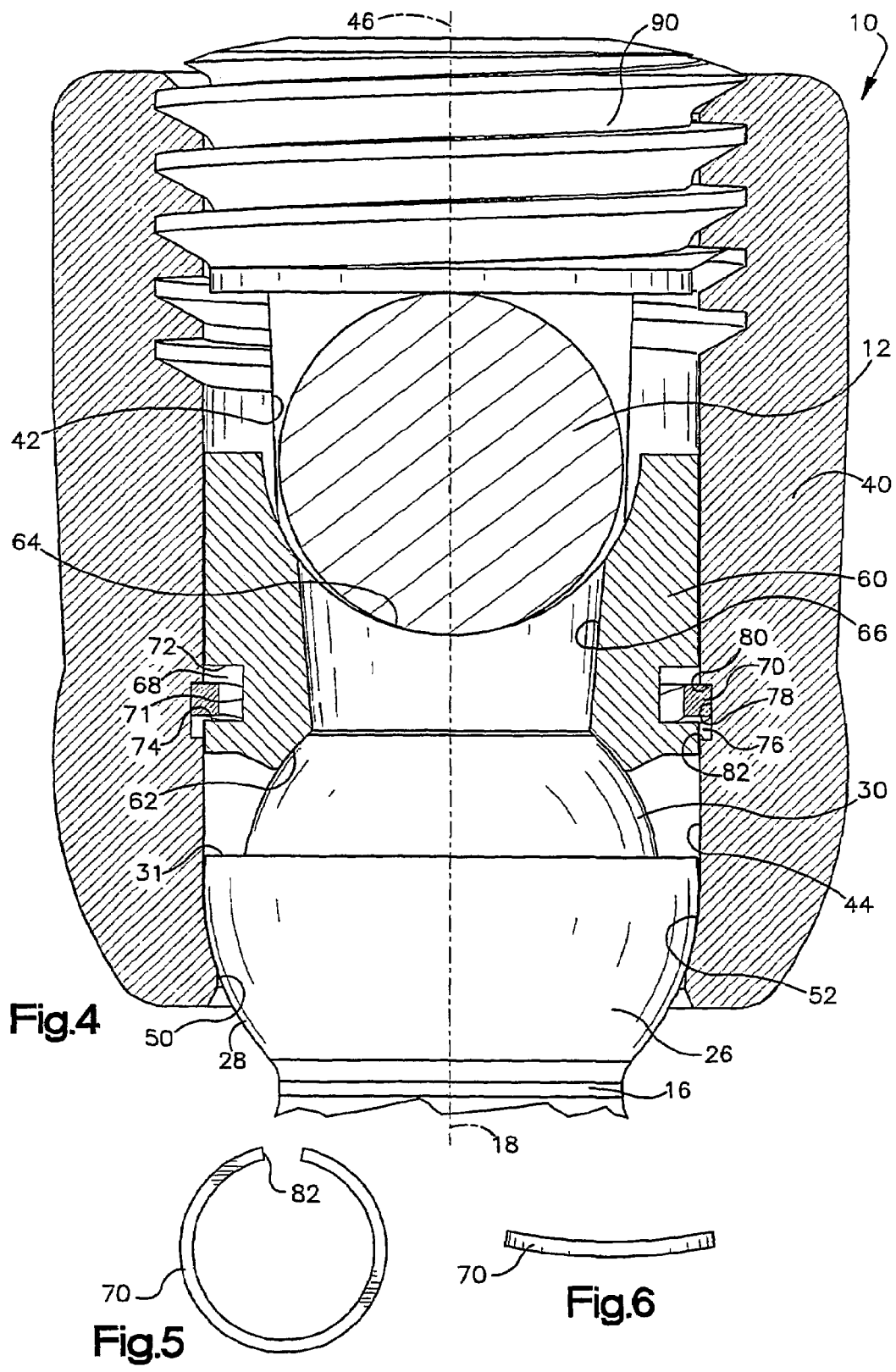

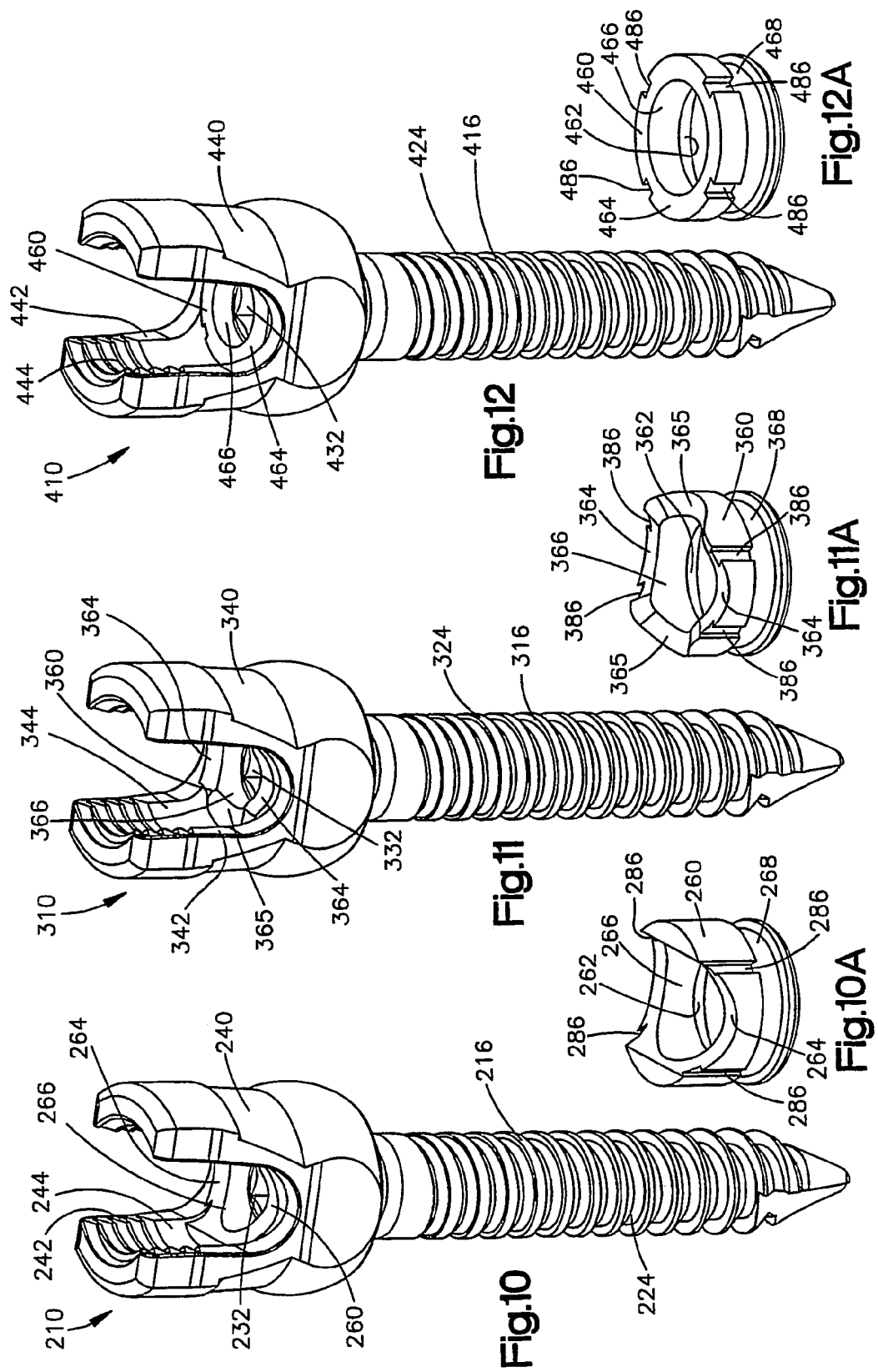

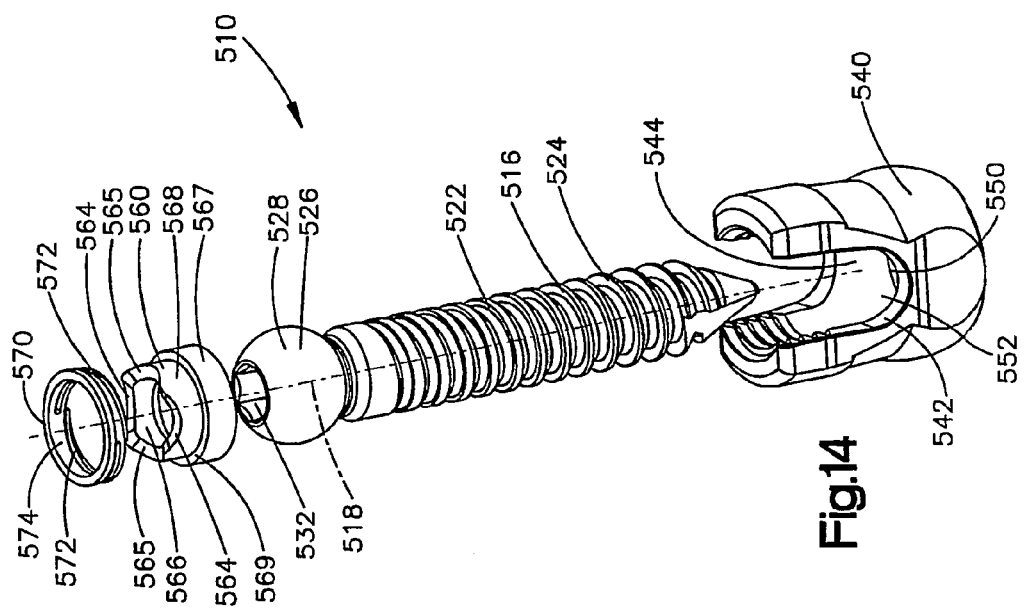
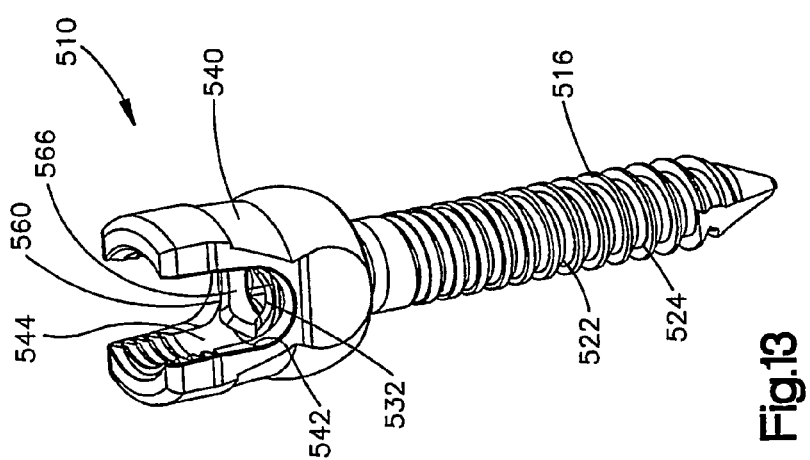

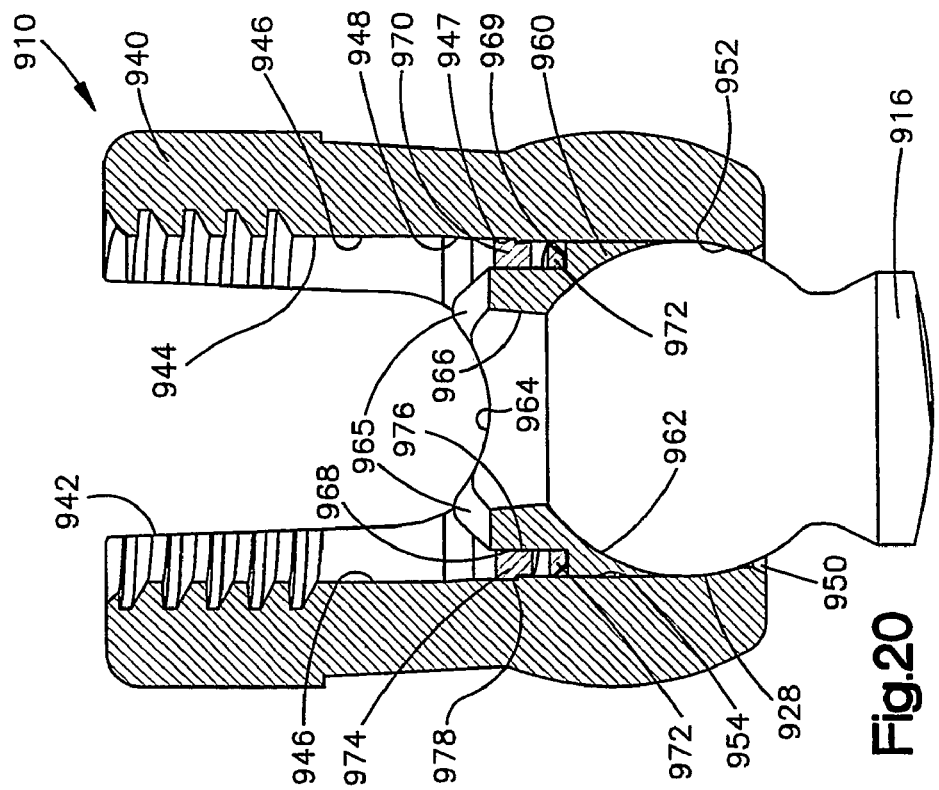
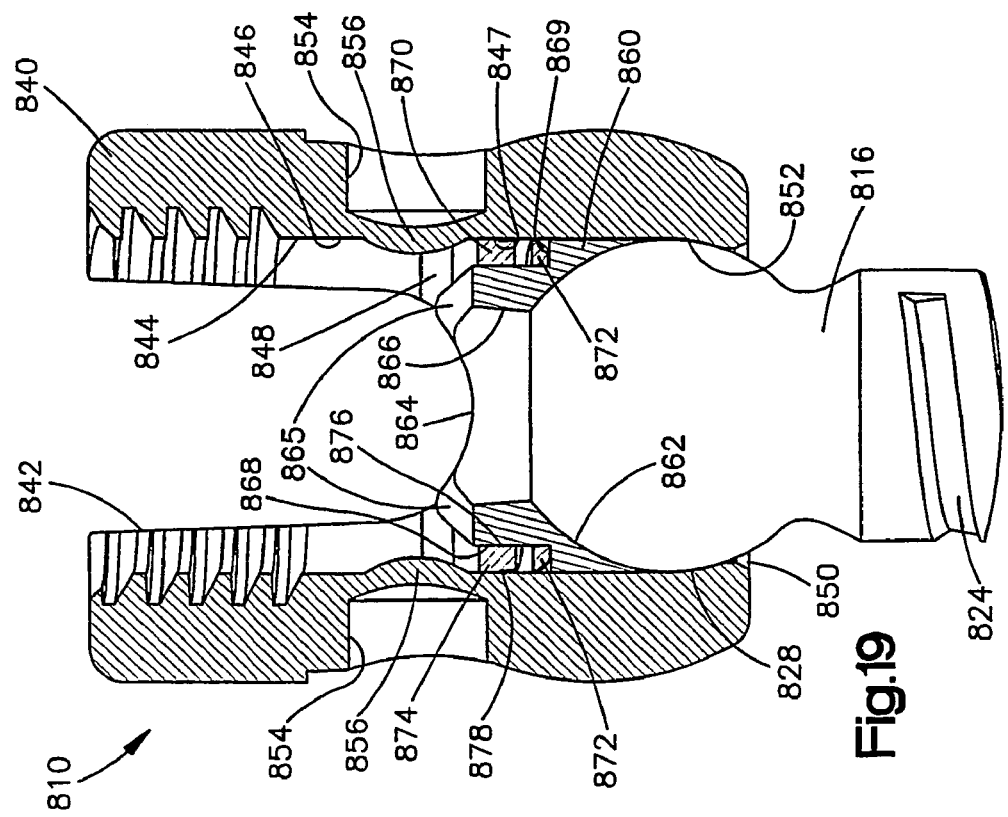

APPARATUS FOR CONNECTING A LONGITUDINAL MEMBER TO A BONE PORTION

RELATED APPLICATIONS

This application is a continuation-in-part of application serial numbers 10/075,668, filed Feb. 13, 2002 and 10/087,489, filed Mar. 1, 2002.

TECHNICAL FIELD

The present invention relates to an apparatus which is used to retain bone portions, such as vertebrae of a spinal column, in a desired spatial relationship.

BACKGROUND OF THE INVENTION

The human spine is configured to maintain an upright posture and, as such, must be capable of supporting substantial weight. Injuries or deformities of the spine may compromise this function. Orthopedic surgery to treat such conditions will often insert implants, for example a metal rod connected to sequential vertebrae via bone screws, to fix the position of the vertebrae and thereby stabilize the spine and augment support.

The first generation of vertebral screws could be connected to a rod in a single orientation ("monoaxial screws"). Variations in anatomy and difficulties in screw placement would frequently result in non-linear placement of screws, so that bending of a spanning rod or the use of special adaptors would often be required to provide a connectable configuration. Such intra-operative reconfiguration can be difficult and is error-prone.

Accordingly, a second generation of vertebral screws was developed which could connect with a rod in multiple orientations ("polyaxial screws"). For example, the fixation element portion of the screw could be pivotally joined to a housing, so that the housing could be oriented to connect with a rod, and then be fixed in place. Examples of patents relating to polyaxial screws include U.S. Pat. Nos. 6,280,442, 6,485,491, U.S. Patent Application Publication No. 2003/0004512, and U.S. Patent Application Publication No. 2001/0001119.

One problem encountered in the use of polyaxial screws is that the housings (or "heads") of most polyaxial pedicle screws are freely movable with respect to the bone screw portion prior to rod insertion and tightening. A surgeon may rotate the housing of the pedicle screw to line up for rod placement, but, once the housing is released, it may move and shift, causing rod placement to be difficult.

The present invention addresses this problem, in that, in one aspect, it provides for polyaxial screws in which the housing is frictionally held to the bone screw. This frictional joint allows the surgeon to place the pedicle screw in the bone and move the housing relative to the bone screw to accept the rod such that once the housing is moved to accept rod placement, it will substantially maintain its position. This feature is especially advantageous for endoscopic pedicle screw placement, where assembly is performed in a confined space. In exemplary embodiments of the invention, the head to bone screw friction can be adjusted to the desired amount. This minimizes tolerances needed during manufacturing and minimizes manufacturing scrap inherent in other designs.

SUMMARY OF THE INVENTION

The present invention relates to polyaxial screws and apparatus comprising such screws which may be used to retain bone portions in a desired spatial relationship. The apparatus includes a longitudinal member (e.g., a rod) connectable with a bone portion. A screw (hereafter referred to as a "fastener") having a longitudinal axis is engageable with the bone portion to connect the longitudinal member to the bone portion. A housing has a first passage configured to receive the longitudinal member. The housing has a second passage with a longitudinal axis extending transverse to the first passage. The fastener extends through an opening in the housing into the second passage and is movable relative to the housing. The longitudinal axis of the fastener is positionable in any one of a plurality of angular positions relative to the longitudinal axis of the second passage.

A spacer received in the second passage of the housing is engageable with the fastener and the longitudinal member. A positioning member applies a force to prevent relative movement between the fastener and the housing when the longitudinal member is disengaged from the spacer and the spacer engages the fastener. The fastener and the housing are manually movable relative to each other against the force when the longitudinal member is disengaged from the spacer and the positioning member applies the force. Accordingly, an advantage of the present invention is that the housing and the fastener can be positioned relative to each other and the member will hold the fastener and the housing in the relative positions before the longitudinal member is connected to the housing. In the absence of a positioning member, the movement of the housing relative to the fixation element is relatively unrestricted, and can prove cumbersome, particularly in minimally invasive procedures performed via a cannula. A clamping mechanism clamps the longitudinal member, the spacer, and the housing to the fastener to prevent movement of the fastener, the housing, and the longitudinal member relative to each other.

In a first embodiment of the present invention the positioning member is a compression member, for example a spring member applying the force to partially or completely restrict relative movement between the fastener and the housing when the longitudinal member is disengaged from the spacer and the spacer engages the fastener. The spring member maintains the spacer in frictional engagement with the fastener and the fastener in frictional engagement with the housing.

In another embodiment of the present invention, the positioning member is a pin member applying a force to partially or completely restrict relative movement between the fastener and the housing when the longitudinal member is disengaged from the spacer and the spacer engages the fastener. The pin member is fixedly connected to the housing and extends from the housing into engagement with the spacer to retain the spacer and the fastener in the housing. The pin member maintains the spacer in frictional engagement with the fastener and the fastener in frictional engagement with the housing.

In another embodiment of the present invention, a retaining ring holds the spring member and the spacer in the housing. The retaining ring is press-fit into the housing so that the amount of force applied by the spring member may be adjusted.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a perspective view of an apparatus constructed in accordance with a first embodiment of the present invention with portions removed for clarity;

FIG. 1A is another perspective view of the apparatus of FIG. 1 with parts removed for clarity;

FIG. 2 is a sectional view of the apparatus of FIG. 1;

FIG. 3 is a part sectional view of the apparatus of FIG. 1;

FIG. 4 is an enlarged sectional view of a portion of the apparatus of FIG. 1;

FIG. 5 is a plan view of a spring member of the apparatus of FIG. 1;

FIG. 6 is a side view of the spring member of FIG. 5;

FIG. 10 is a perspective view of an apparatus constructed in accordance with another embodiment of the present invention with portions removed for clarity;

FIG. 10A is a perspective view of a spacer of the apparatus of FIG. 10;

FIG. 11 is a perspective view of an apparatus constructed in accordance with another embodiment of the present invention with portions removed for clarity;

FIG. 11A is a perspective view of a spacer of the apparatus of FIG. 11;

FIG. 12 is a perspective view of an apparatus constructed in accordance with another embodiment of the present invention with portions removed for clarity;

FIG. 12A is a perspective view of a spacer of the apparatus of FIG. 12;

FIG. 13 is a perspective view of an apparatus constructed in accordance with another embodiment of the present invention with portions removed for clarity;

FIG. 14 is an exploded view of the apparatus of FIG. 13;

FIG. 19 is a sectional view of an apparatus constructed in accordance with another embodiment of the present invention;

FIG. 20 is a sectional view of an apparatus constructed in accordance with another embodiment of the present invention.

DESCRIPTION OF THE INVENTION

Figure 7:
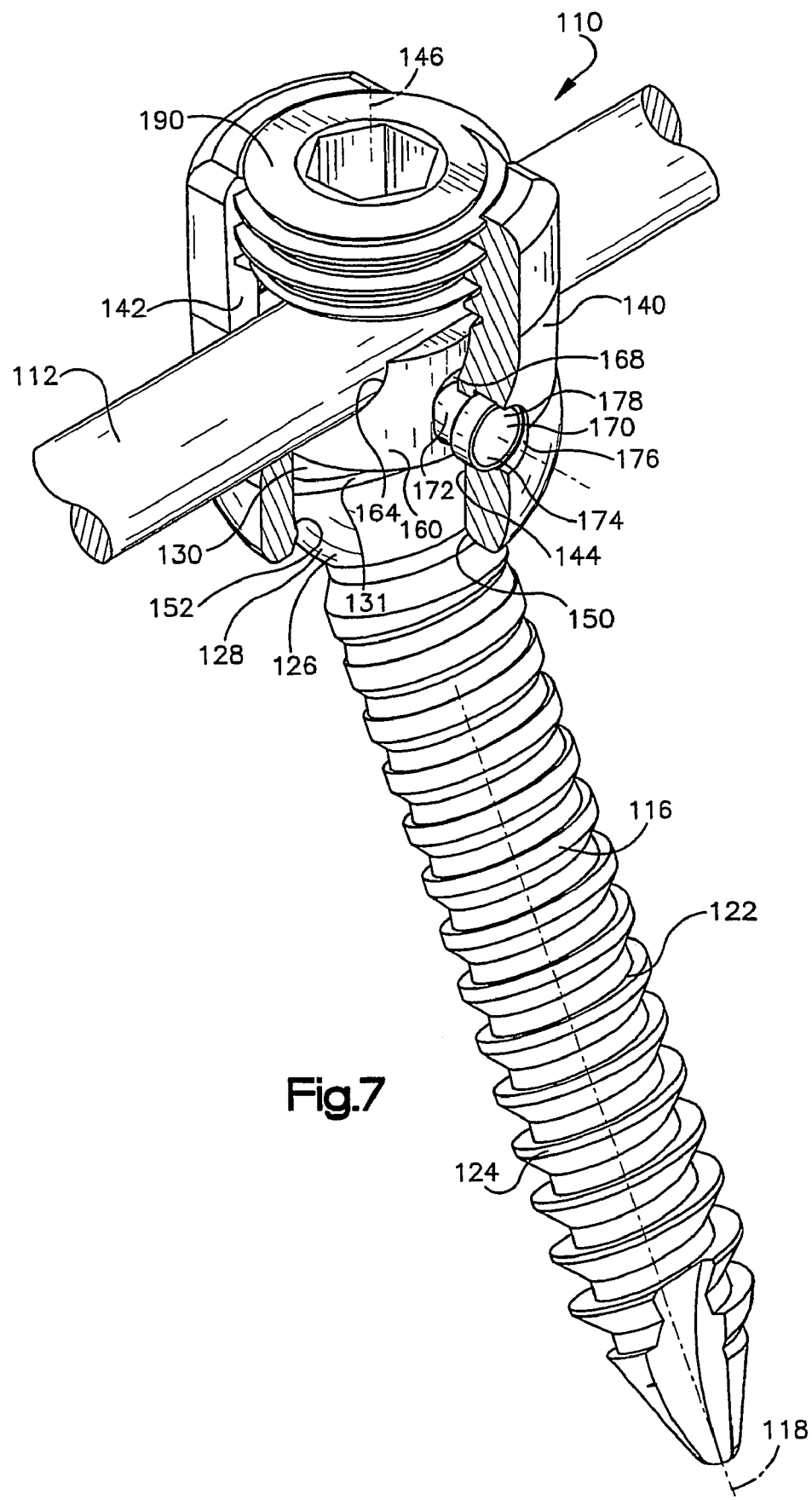
FIG. 7 is a perspective view of an apparatus constructed in accordance with another embodiment of the present invention with portions removed for clarity.

The present invention is directed to an apparatus for retaining bone portions, such as vertebrae of a spinal column, in a desired spatial relationship. FIGS. 1–4 illustrate an apparatus 10 constructed according to a first embodiment of the present invention. The apparatus 10 includes a surgically implantable longitudinal member or rod 12 for maintaining bone portions, such as vertebrae of a spinal column, in a desired spatial relationship. The member 12 is connected with vertebrae of the spinal column by fasteners 16.

The rod 12 is made of a suitable biocompatible material and has a length which is at least sufficient to enable the rod to span at least two vertebrae. Of course, the length of the rod 12 in any particular installation will depend upon the condition to be corrected and the number of vertebrae to be held in a desired spatial relationship relative to each other by the rod.

The rod 12 (FIGS. 1–3) is connected to a respective vertebra by the fastener 16 made of a suitable biocompatible material. The fastener 16 has a longitudinal axis 18 and a threaded end portion 22 having a course thread convolution 24 which engages the vertebra. A second end portion 26 of the fastener 16 is provided with a first part spherical surface 28. The second end portion 26 of the fastener 16 also includes a second part spherical surface 30 having a diameter less than a diameter of the first part spherical surface 28. A radially extending shoulder 31 extends between the part spherical surfaces 28 and 30. A recess 32 (FIG. 2) is provided on the end portion 26 of the fastener 16. The recess 32 receives a tool (not shown) that applies torque to the fastener 16 to turn the thread convolution 24 into the vertebra.

The fastener 16 (FIGS. 1–4) extends into a housing 40 that interconnects the rod 12 and the fastener 16. The housing 40 (FIG. 2) has a first passage 42 through which the rod 12 extends. The housing 40 has a second passage 44 with a longitudinal axis 46 that extends transverse to the first passage 42. The fastener 16 extends through an opening 50 in the housing 40 and into the second passage 44. The first part spherical surface 28 of the fastener 16 engages a concave part spherical surface 52 of the housing 40. Accordingly, the fastener 16 is universally pivotable relative to the housing 40 so that the longitudinal axis 18 of the fastener 16 is positionable in any one of a plurality of angular positions relative to the longitudinal axis 46 of the passage 44.

A spacer 60 is housed in the second passage 44 of the housing 40. The spacer 60 (FIGS. 2–4) has a concave part spherical surface 62 that engages the part spherical surface 30 of the fastener 16. The shoulder 31 on the fastener 16 is engageable with the spacer 60 to limit the relative movement between the fastener and the housing 40. The spacer 60 also has a concave part cylindrical surface 64 that engages the rod 12. The spacer 60 has an opening 66 through which the tool (not shown) extends to engage the recess 32 in the fastener 16. The tool extends through the opening 66 to apply torque to the fastener 16 and connect the fastener to the vertebra.

The spacer 60 includes two tabs 67 (FIGS. 1, 1A, and 2) that are engageable with the housing 40. The tabs 67 engage surfaces of the housing 40 that define the passage 42 to restrict rotation of the spacer 60 within the housing 40. The width of the tabs 67 is selected as smaller than the width of the passage 42 to permit the spacer 60 to rotate slightly (preferably at least 10° and less than 30°) relative to the housing 40 when the rod 12 is disengaged from the spacer, but prevent sufficient rotation to completely move the concave portion 64 of the spacer outside of passage 42. The tabs 67 are spaced from the surfaces of the housing 40 that define the passage 42 when the rod 12 is disengaged from the spacer 60 to permit axial movement of the spacer relative to the housing. The tabs 67 may be spaced from the surfaces of the housing 40 that define the passage 42 when the rod 12 is in engagement with the spacer 60, as seen in FIG. 2.

The spacer 60 (FIG. 4) has a circumferential groove 68 for receiving a compressible positioning member such as a spring member 70. The groove 68 is defined by an axially extending cylindrical surface 71. An upper surface 72 extends radially outward from the cylindrical surface 71. A lower surface 74 extends radially outward from the cylindrical surface 71 and generally parallel to the upper surface 72.

The housing 40 includes a circumferential groove 76 for receiving the spring member 70 so that the spring member extends from the groove 68 in the spacer 60 to the groove in the housing. The groove 76 is defined by an axially extending cylindrical surface 78. An upper surface 80 extends radially inward from the cylindrical surface 78. A lower surface 82 extends radially inward from the cylindrical surface 78 and generally parallel to the upper surface 80.

The spring member 70 (FIGS. 5 and 6) is a ring having a gap 82. It is contemplated that the spring member 70 may be any desired spring member, such as a coil spring. The gap 82 permits the spring member 70 to radially contract and expand. The spring member 70 has an arched shape, as viewed in FIG. 6, when the spring member 70 is disengaged from the spacer 60 and the housing 40. When the spring member 70 is received in the grooves 68 and 76 (FIG. 4), the spring member engages the lower surface 74 on the spacer 60 and the upper surface 80 on the housing 40.

The spring member 70 applies an axial force to the spacer 60 to partially or completely restrict relative movement between the fastener 16 and the housing 40 when the rod 12 is disengaged from the spacer and the spacer engages the fastener (the phrase, "completely restrict" as used herein means that there is essentially no relative movement, and the phrase "partially restrict" means that movement is inhibited but that some movement is possible). The spring member 70 urges the spacer 60 axially toward the fastener 16 and the part spherical surface 52 of the housing 40 against the part spherical surface 28 of the fastener. The part spherical surface 62 of the spacer 60 frictionally engages the part spherical surface 30 of the fastener 16 and the part spherical surface 28 of the fastener frictionally engages the part spherical surface 52 of the housing 40. The fastener 16 and the housing 40 are manually movable relative to each other by a surgeon when the rod 12 is disengaged from the spacer 60 and the spring member 70 applies the axial force. The force applied by the spring member 70 may be overcome by the surgeon to move the housing 40 relative to the fastener 16. Accordingly, the housing 40 can be positioned relative to the fastener 16 and held in position relative to the fastener by the spring member 70 without the rod 12 engaging the spacer 60. It is contemplated that any compressible member could be used to apply the force to the fastener 16 to prevent relative movement between the fastener and the housing 40 when the rod 12 is disengaged from the spacer 60.

The spacer 60 has four axially extending slots 86, one of which is shown in FIG. 1. The slots 86 intersect the groove 68. A tool (not shown) has prongs that extend through the slots 86 and into engagement with the spring member 70. The tool grasps the spacer 60 and the spring member 70 for inserting the spacer and the spring member into the housing 40. The prongs of the tool engage the spring member 70 to radially contract the spring member into the groove 68 in the spacer 60. The prongs hold the spring member 70 in the radially contracted condition in the groove 68 while the spacer 60 and spring member are being inserted into the housing 40. Once the spacer 60 engages the fastener 16, the prongs are removed from the slots 86 and the spring member 70 radially expands into the groove 71 in the housing 40. Although the spacer 60 is described as having four slots 86, the spacer could have any number of slots and the tool would have the same number of prongs as the spacer has slots.

A clamping mechanism or set screw 90 (FIGS. 1–4) threadably engages the housing 40. The set screw 90 and the housing 40 have a German standard DIN513 buttress thread. It is contemplated that the set screw 90 and the housing 40 could have any desired thread formation. The set screw 90 engages and applies a force to the rod 12 to press the rod against the spacer 60 and the spacer against the fastener 16. The set screw 90 clamps the rod 12, the spacer 60, and the housing 40 to the fastener 16 to prevent movement of the fastener relative to the housing. The force applied by the set screw 90 cannot be overcome by the surgeon to move the housing 40 relative to the fastener 16.

The apparatus 10 is assembled by inserting the fastener 16 through the opening 50 in the housing 40 so that the part spherical surface 28 of the fastener engages the part spherical surface 52 of the housing. The spacer 60 and the spring member 70 are inserted into the housing 40 by radially compressing the spring member into the groove 68 in the spacer. The spacer 60 and the spring member 70 are inserted into the second passage 44 until the part spherical surface 62 of the spacer engages the part spherical surface 30 of the fastener 16. The spring member 70 is released and expands radially into the groove 76 in the housing 40.

A tool is inserted through the opening 66 in the spacer 60 and into the recess 32 in the fastener 16. Torque is applied to the fastener 16 to turn the thread convolution 24 into the vertebra. Once the fastener 16 is connected with the vertebra, the housing 40 can be positioned relative to the fastener. The spring member 70 maintains the position of the housing 40 relative to the fastener 16 while the rod 12 is disengaged from the spacer 60. Once the housing 40 is positioned relative to the fastener 16, the rod 12 is placed into the passage 42 and in engagement with the spacer 60. The set screw 90 is threaded into the housing 40 and into engagement with the rod 12. The set screw 90 clamps the rod 12, the spacer 60, and the housing 40 to the fastener 16 to prevent movement of the fastener relative to the housing. Alternatively, the fastener 16 may be connected to the vertebra prior to the spacer 60 and the spring member 70 being inserted into the housing 40.

Figure 8:
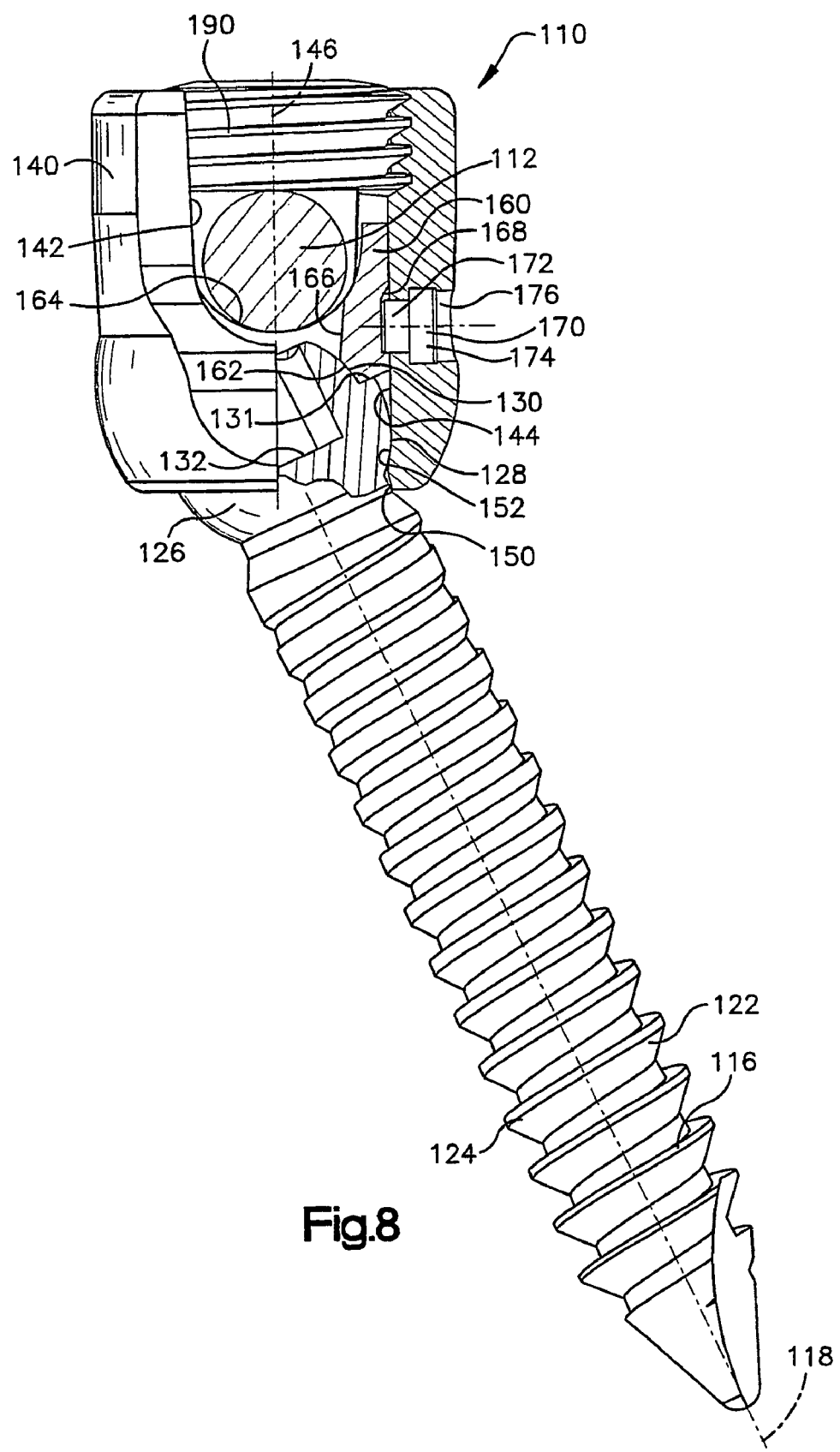
FIG. 8 is a part sectional view of the apparatus of FIG. 7.
Figure 9:
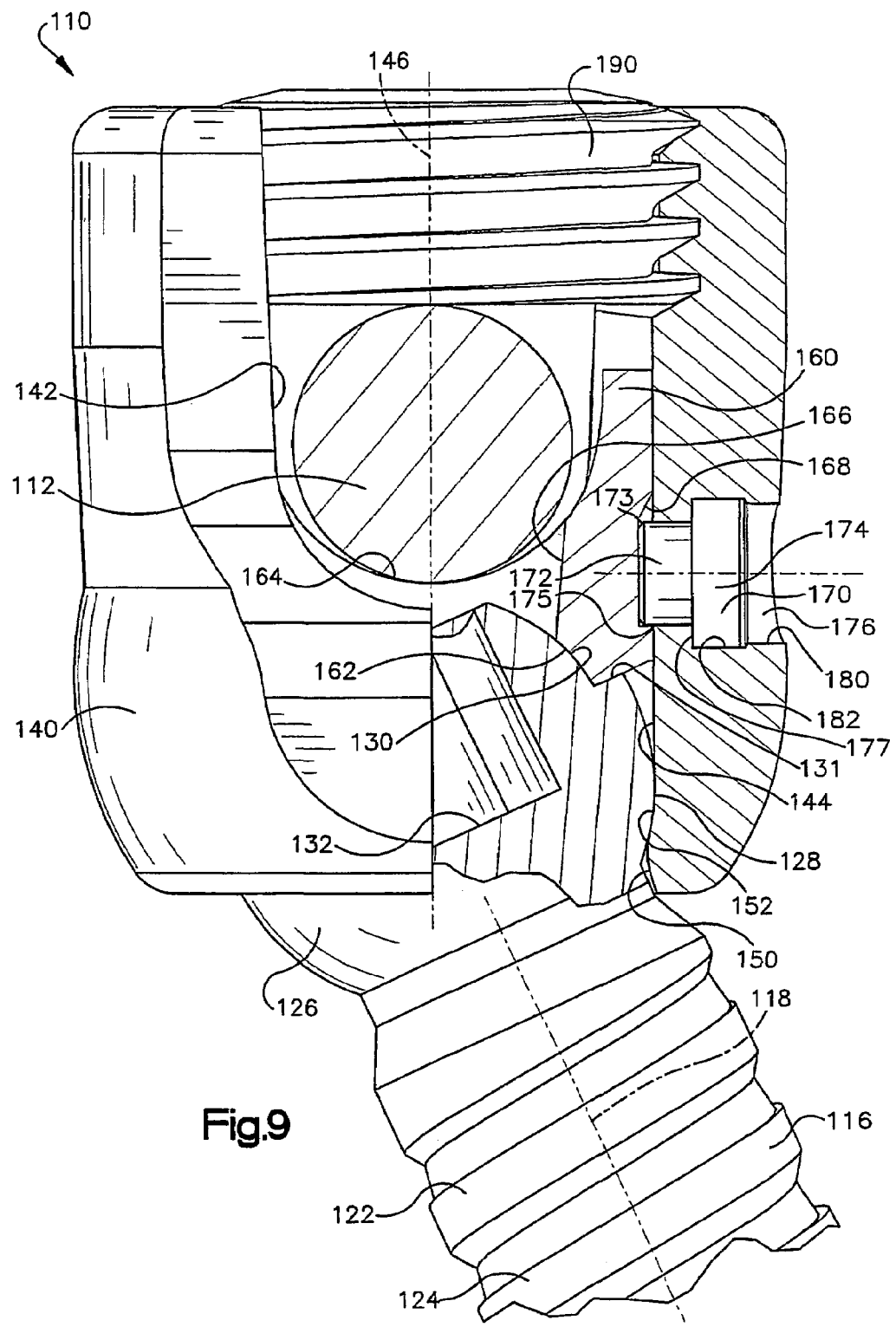
FIG. 9 is an enlarged part sectional view of a portion of the apparatus of FIG. 7.

FIGS. 7–9 illustrate an apparatus 110 constructed according to another embodiment of the present invention. The apparatus 110 includes a surgically implantable longitudinal member or rod 112 for maintaining bone portions, such as vertebrae of a spinal column, in a desired spatial relationship. The rod 112 is connected with vertebrae of the spinal column by fasteners 116.

The rod 112 is made of a suitable biocompatible material and has a length which is at least sufficient to enable the rod to span at least two vertebrae. Of course, the length of the rod 112 in any particular installation will depend upon the condition to be corrected and the number of vertebrae to be held in a desired spatial relationship relative to each other by the rod.

The rod 112 is connected to a respective vertebra by the fastener 116 made of a suitable biocompatible material. The fastener 116 has a longitudinal axis 118 and a threaded end portion 122 having a course thread convolution 124 which engages the vertebra. A second end portion 126 (FIGS. 8–9) of the fastener 116 is provided with a first part spherical surface 128. The second end portion 126 of the fastener 116 also includes a second part spherical surface 130 having a diameter less than a diameter of the first part spherical surface 128. A radially extending shoulder 131 extends between the part spherical surfaces 128 and 130. A recess 132 (FIGS. 8–9) is provided on the end portion 126 of the fastener 116. The recess 132 receives a tool (not shown) that applies torque to the fastener 116 to turn the thread convolution 124 into the vertebra.

The fastener 116 (FIGS. 7–9) extends into a housing 140 that interconnects the rod 112 and the fastener 116. The housing 140 has a first passage 142 through which the rod 112 extends. The housing 140 has a second passage 144 with a longitudinal axis 146 that extends transverse to the first passage 142. The fastener 116 extends through an opening 150 in the housing 140 and into the second passage 144. The first part spherical surface 128 of the fastener 116 engages a concave part spherical surface 152 of the housing 140. Accordingly, the fastener 116 is universally pivotable relative to the housing 140 so that the longitudinal axis 118 of the fastener 116 is positionable in any one of a plurality of angular positions relative to the longitudinal axis 146 of the passage 144.

A spacer 160 is received in the second passage 144 of the housing 140. The spacer 160 (FIGS. 8–9) has a concave part spherical surface 162 that engages the part spherical surface 130 of the fastener 116. The spacer 160 also has a concave part cylindrical surface 164 that engages the rod 112. The spacer 160 has an opening 166 through which the tool (not shown) extends to engage the recess 132 in the fastener 116. The tool extends through the opening 166 to apply torque to the fastener 116 and connect the fastener to the vertebra.

The spacer 160 has a pair of axially extending grooves 168, one of which is shown in FIGS. 7–9. The grooves 168 are located on diametrically opposite sides of the spacer 160. A pair of positioning members or pin members 170, one of which is shown in FIGS. 7–9, extend transverse to the longitudinal axis 146 of the passage 144 and through the housing 140 into the grooves 168 and into engagement with the spacer 160. The pin members 170 retain the spacer 160 and the fastener 116 in the housing 140. The pin members 170 also restrict rotation of the spacer 160 relative to the housing 140. Although a pair of axially extending grooves 168 and a pair of pin members 170 are described, it is contemplated that the spacer 160 could have only one groove and only one pin member could extend into the groove, or any number of grooves and pins could be used.

The pin members 170 are identical and, therefore, only one pin member will be described in detail. The pin member 170 has a first cylindrical end portion 172 that extends into the groove 168 and engages the spacer 160. The end portion 172 of the pin member 170 has a frustoconical or tapered surface 173. The tapered surface 173 engages a lower axial edge 175 that defines the groove 168 as the pin member 170 is being inserted through the housing 140 to urge the spacer axially toward the fastener 116. The pin member 170 urges the spacer 160 into frictional engagement with the fastener 116 and the fastener into frictional engagement with the housing 140. It is contemplated that the pin member 170 may not urge the spacer 160 axially toward the fastener 116 and only retain the spacer and the fastener in the housing 140.

A second cylindrical end portion or head 174 of the pin member 170 is located in a cylindrical opening 176 in the housing 140. The head 174 has a diameter greater than a diameter of the end portion 172. Accordingly, the pin member 170 (FIG. 9) has a shoulder surface 177 extending perpendicular to the axis of the pin member 170 on the head 174. The shoulder surface 177 engages the housing 140 to limit the distance that the pin member 170 extends into the housing 140.

The head 174 of the pin member 170 has a conical recess 178 (FIG. 7) for receiving a tool (not shown), such as a center punch, to deform the head 174 into engagement with the housing 140. The opening 176 (FIG. 9) in the housing 140 has a radially outer portion 180 with a diameter slightly smaller than a diameter of a radially central portion 182 of the opening. The head 174 of the pin member 170 is received in the radially central portion 182 of the opening 176. The material of the head 174 is deformed into tight engagement with the material of the housing defining the central portion 182 of the opening 176 so that the diameter of the head is larger than the diameter of the radially outer portion 180 of the opening 176. Accordingly, the pin member 170 is fixedly connected to the housing 140. Although the pin member 170 is described as being deformed into engagement with the housing 140, it is contemplated that the pin member could be press-fit into the housing or otherwise suitably fixed in the housing.

The pin members 170 engage the housing 140 and the spacer 160 to retain the spacer and the fastener in the housing 140. The pin members 170 also apply an axial force to the spacer 160 to prevent relative movement between the fastener 116 and the housing 140 when the rod 112 is disengaged from the spacer and the spacer engages the fastener. The pin members 170 hold the part spherical surface 162 of the spacer 160 in frictional engagement with the part spherical surface 130 of the fastener 116 and the part spherical surface 128 of the fastener in frictional engagement with the part spherical surface 152 of the housing 140. The frictional engagements are effective to maintain the housing 140 and the fastener 116 in position when the rod 112 is disengaged from the spacer. However, the fastener 116 and the housing 140 are manually movable relative to each other by a surgeon manually overcoming the frictional engagements when the rod 112 is disengaged from the spacer 160 and the pin members 170 engage the spacer. Accordingly, the housing 140 can be positioned relative to the fastener 116 and held in position relative to the fastener by the pin members 170 without the rod 112 engaging the spacer 160. Furthermore, the spacer 160 and the fastener 116 are retained in the housing 140 by the pin members 170 and with the rod 112 disengaged from the spacer.

A clamping mechanism or set screw 190 (FIGS. 7–9) threadably engages the housing 140. The set screw 190 and the housing 140 have a German standard DIN513 buttress thread. It is contemplated that the housing 140 and the set screw 190 could have any desired thread formation. The set screw 190 engages the rod 112 to press the rod against the spacer 160 and the spacer against the fastener 116. The set screw 190 clamps the rod 112, the spacer 160, and the housing 140 to the fastener 116 to prevent movement of the fastener relative to the housing.

The apparatus 110 is assembled by inserting the fastener 116 through the opening 150 in the housing 140 so that the part spherical surface 128 of the fastener engages the part spherical surface 152 of the housing. The spacer 160 is inserted into the second passage 144 of the housing 140 until the part spherical surface 162 of the spacer engages the part spherical surface 130 of the fastener 116. The pin members 170 are inserted into the openings 176 in the housing 140 until the end portions 172 extend into the grooves 168 in the spacer 160 and engage the spacer. The tapered surfaces 173 of the pin members 170 engage the edges 175 to urge the spacer 160 axially toward the fastener 116. The heads 174 of the pins 170 are deformed to fixedly connect the pins to the housing 140.

A tool is inserted through the opening 166 in the spacer 160 and into the recess 132 in the fastener 116. Torque is applied to the fastener 116 to turn the thread convolution 124 into the vertebra. Once the fastener 116 is connected with the vertebra, the housing 140 can be positioned relative to the fastener. The pin members 170 and the above described frictional engagements maintain the position of the housing 140 relative to the fastener 116 while the rod 112 is disengaged from the spacer 160. Once the housing 140 is positioned relative to the fastener 116 as desired by the surgeon, the rod 112 is placed into the passage 142 and in engagement with the spacer 160. The set screw 190 is threaded into the housing 140 and into engagement with the rod 112. The set screw 190 clamps the rod 112, the spacer 160, and the housing 140 to the fastener 116 to prevent movement of the fastener relative to the housing.

It is contemplated that the pin members 170 could be inserted into the housing 140 prior to the spacer 160 being inserted into the housing. If the spacer 160 is inserted after the pin members 170, the spacer would have L-shaped grooves with axially extending portions and circumferentially extending portions. The spacer 160 would be inserted into the housing 140 with the axially extending portions aligned with the pin members 170 until the pin members extend into the circumferentially extending portions. The spacer 160 would be rotated relative to the housing 140 until the pin members 170 are located in ends of the circumferentially extending portions of the grooves opposite from the axially extending portions.

An apparatus 210 constructed according to another embodiment of the present invention is illustrated in FIGS. 10 and 10A. The apparatus 210 is substantially similar to the apparatus 10 illustrated in FIGS. 1–6. Accordingly, the apparatus 210 will not be described in detail.

The apparatus 210 includes a fastener 216 (FIG. 10) for connecting a surgically implantable longitudinal member or rod (not shown) to bone portions, such as vertebrae of a spinal column, to maintain the vertebrae in a desired spatial relationship. The rod and the fastener 216 are identical to the rod 12 and the fastener 16 illustrated in FIGS. 1–4. Accordingly, the rod and the fastener 216 will not be described in detail.

The fastener 216 extends into a housing 240 that interconnects the rod and the fastener. The housing 240 is identical to the housing 40 illustrated in FIGS. 1–4. Accordingly, the housing 240 will not be described in detail. A part spherical surface of the fastener 216 engages a concave part spherical surface of the housing 240 so that the fastener is universally pivotable relative to the housing and an axis of the fastener is positionable in any one of a plurality of angular positions relative to an axis of a passage 244 of the housing.

A spacer 260 (FIGS. 10 and 10A) is housed in the passage 244 of the housing 240. The spacer 260 has a concave part spherical surface 262 that engages a part spherical surface of the fastener 216. The spacer 260 also has a concave part cylindrical surface 264 that engages the rod when the surface 264 is aligned with a passage 242 in the housing 240. The spacer 260 has an opening 266 through which a tool (not shown) extends to engage a recess 232 in the fastener 216. The tool extends through the opening 266 to apply torque to the fastener 216 and connect the fastener to the vertebra.

The spacer 260 is substantially similar to the spacer 60 illustrated in FIGS. 1–4. However, the spacer 260 does not include tabs 67.

The spacer 260 (FIG. 10A) has a circumferential groove 268 for receiving a compressible positioning member such as a spring member (not shown). The housing 240 includes a circumferential groove (not shown) for receiving the spring member so that the spring member extends from the groove 268 in the spacer 260 to the groove in the housing. The spring member may be identical to the spring member 70 illustrated in FIGS. 1–6, or may be a functionally equivalent compressible element.

When the spring member is received in the groove 268 in the spacer 260 and the groove in the housing 240, the spring member applies an axial force to the spacer 260 to prevent relative movement between the fastener 216 and the housing 240 when the rod is disengaged from the spacer and the spacer engages the fastener. The spring member urges the spacer 260 axially toward the fastener 216 so that the part spherical surface 262 of the spacer 260 frictionally engages a part spherical surface of the fastener 216 and another part spherical surface of the fastener frictionally engages the concave part spherical surface of the housing 240. The fastener 216 and the housing 240 are manually movable relative to each other by a surgeon when the rod is disengaged from the spacer 260 and the spring member applies the axial force. The force applied by the spring member may be overcome by the surgeon to move the housing 240 relative to the fastener 216. Accordingly, the housing 240 can be positioned relative to the fastener 216 and held in position relative to the fastener by the spring member without the rod engaging the spacer 260.

The spacer 260 has four axially extending slots 286. The slots 286 intersect the groove 268. A tool (not shown) has four prongs that extend through the slots 286 and into engagement with the spring member. The tool grasps the spacer 260 and the spring member for inserting the spacer and the spring member into the housing 240. The prongs of the tool engage the spring member to radially contract the spring member into the groove 268 in the spacer 260. The prongs hold the spring member in the radially contracted condition in the groove 268 while the spacer 260 and spring member are being inserted into the housing 240. Once the spacer 260 engages the fastener 216, the prongs are removed from the slots 286 and the spring member radially expands into the groove in the housing 240. Although the spacer 260 is described as having four slots 286, the spacer could have any number of slots and the tool would have the same number of prongs as the spacer has slots.

A clamping mechanism or set screw (not shown) threadably engages the housing 240. The clamping mechanism is identical to the clamping mechanism 90 illustrated in FIGS. 1–4. The set screw engages and applies a force to the rod to press the rod against the spacer 260 and the spacer against the fastener 216. The set screw clamps the rod, the spacer 260, and the housing 240 to the fastener 216 to prevent movement of the fastener relative to the housing. The force applied by the set screw cannot be overcome by the surgeon to move the housing 240 relative to the fastener 216.

The apparatus 210 is assembled by inserting the fastener 216 through an opening in the housing 240 so that a part spherical surface of the fastener engages the concave part spherical surface of the housing. The spacer 260 and the spring member are inserted into the housing 240 by radially compressing the spring member into the groove 268 in the spacer. The spacer 260 and the spring member are inserted into the passage 244 in the housing 240 until the part spherical surface 262 of the spacer engages a part spherical surface of the fastener 216. The spring member is released and expands radially into the groove in the housing 240.

A tool is inserted through the opening 266 in the spacer 260 and into the recess 232 in the fastener 216. Torque is applied to the fastener 216 to turn a thread convolution 224 into the vertebra. Once the fastener 216 is connected with the vertebra, the housing 240 can be positioned relative to the fastener. The spring member maintains the position of the housing 240 relative to the fastener 216 while the rod is disengaged from the spacer 260. Once the housing 240 is positioned relative to the fastener 216, the spacer 260 is rotated relative to the housing 240 to align the part cylindrical surface 264 of the spacer with the passage 242 in the housing 240. The rod is placed into the passage 242 in the housing 240 and in engagement with the spacer 260. The set screw is threaded into the housing 240 and into engagement with the rod. The set screw clamps the rod, the spacer 260, and the housing 240 to the fastener 216 to prevent movement of the fastener relative to the housing. Alternatively, the fastener 216 may be connected to the vertebra prior to the spacer 260 and the spring member being inserted into the housing 240.

An apparatus 310 constructed according to another embodiment of the present invention is illustrated in FIGS. 11 and 11A. The apparatus 310 is substantially similar to the apparatus 10 illustrated in FIGS. 1–6. Accordingly, the apparatus 310 will not be described in detail.

The apparatus 310 includes a fastener 316 (FIG. 11) for connecting a surgically implantable longitudinal member or rod (not shown) to bone portions, such as vertebrae of a spinal column, to maintain the vertebrae in a desired spatial relationship. The rod and the fastener 316 are identical to the rod 12 and the fastener 16 illustrated in FIGS. 1–4. Accordingly, the rod and the fastener 316 will not be described in detail.

The fastener 316 extends into a housing 340 that interconnects the rod and the fastener. The housing 340 is identical to the housing 40 illustrated in FIGS. 1–4. Accordingly, the housing 340 will not be described in detail. A part spherical surface of the fastener 316 engages a concave part spherical surface of the housing 340 so that the fastener is universally pivotable relative to the housing and an axis of the fastener is positionable in any one of a plurality of angular positions relative to an axis of a passage 344 of the housing.

A spacer 360 (FIGS. 11 and 11A) is housed in the passage 344 of the housing 340. The spacer 360 has a concave part spherical surface 362 that engages a part spherical surface of the fastener 316. The spacer 360 has a pair of diametrically opposed concave part cylindrical surfaces 364. The surfaces 364 engage the rod when the surfaces 364 are aligned with a passage 342 in the housing 340 through which the rod extends. The spacer 360 also includes a pair of diametrically opposed concave part cylindrical surfaces 365. The surfaces 365 engage the rod when the surfaces 365 are aligned with the passage 342. The surfaces 364 are located 90° from the surfaces 365. Accordingly, the spacer 360 has a plurality of rotational positions relative to the housing 340 for receiving the longitudinal member. Although the spacer 360 is shown as having two sets of diametrically opposed cylindrical surfaces 364 and 365, it is contemplated that the spacer may have any number of sets of cylindrical surfaces. The spacer 360 has an opening 366 through which a tool (not shown) extends to engage a recess 332 in the fastener 316. The tool extends through the opening 366 to apply torque to the fastener 316 and to connect the fastener to the vertebra.

The spacer 360 (FIG. 11A) has a circumferential groove 368 for receiving a compressible member such as a spring member (not shown). The housing 340 includes a circumferential groove (not shown) for receiving the spring member so that the spring member extends from the groove 368 in the spacer 360 to the groove in the housing. The spring member is identical to the spring member 70 illustrated in FIGS. 1–6.

When the spring member is received in the groove 368 in the spacer 360 and the groove in the housing 340, the spring member applies an axial force to the spacer 360 to prevent relative movement between the fastener 316 and the housing 340 when the rod is disengaged from the spacer and the spacer engages the fastener. The spring member urges the spacer 360 axially toward the fastener 316 so that the part spherical surface 362 of the spacer 360 frictionally engages a part spherical surface of the fastener 316 and another part spherical surface of the fastener frictionally engages the concave part spherical surface of the housing 340. The fastener 316 and the housing 340 are manually movable relative to each other by a surgeon when the rod is disengaged from the spacer 360 and the spring member applies the axial force. The force applied by the spring member may be overcome by the surgeon to move the housing 340 relative to the fastener 316. Accordingly, the housing 340 can be positioned relative to the fastener 316 and held in position relative to the fastener by the spring member without the rod engaging the spacer 360.

The spacer 360 has four axially extending slots 386. The slots 386 intersect the groove 368. A tool (not shown) has four prongs that extend through the slots 386 and into engagement with the spring member. The tool grasps the spacer 360 and the spring member for inserting the spacer and the spring member into the housing 340. The prongs of the tool engage the spring member to radially contract the spring member into the groove 368 in the spacer 360. The prongs hold the spring member in the radially contracted condition in the groove 368 while the spacer 360 and spring member are being inserted into the housing 340. Once the spacer 360 engages the fastener 316, the prongs are removed from the slots 386 and the spring member radially expands into the groove in the housing 340. Although the spacer 360 is described as having four slots 386, the spacer could have any number of slots and the tool would have the same number of prongs as the spacer has slots.

A clamping mechanism or set screw (not shown) threadably engages the housing 340. The claming mechanism is identical to the clamping mechanism 90 illustrated in FIGS. 1–4. The set screw engages and applies a force to the rod to press the rod against the spacer 360 and the spacer against the fastener 316. The set screw clamps the rod, the spacer 360, and the housing 340 to the fastener 316 to prevent movement of the fastener relative to the housing. The force applied by the set screw cannot be overcome by the surgeon to move the housing 340 relative to the fastener 316.

The apparatus 310 is assembled by inserting the fastener 316 through an opening in the housing 340 so that a part spherical surface of the fastener engages the concave part spherical surface of the housing. The spacer 360 and the spring member are inserted into the housing 340 by radially compressing the spring member into the groove 368 in the spacer. The spacer 360 and the spring member are inserted into the passage 344 in the housing 340 until the part spherical surface 362 of the spacer engages a part spherical surface of the fastener 316. The spring member is released and expands radially into the groove in the housing 340.

A tool is inserted through the opening 366 in the spacer 360 and into the recess 332 in the fastener 316. Torque is applied to the fastener 316 to turn a thread convolution 324 into the vertebra. Once the fastener 316 is connected with the vertebra, the housing 340 can be positioned relative to the fastener. The spring member maintains the position of the housing 340 relative to the fastener 316 while the rod is disengaged from the spacer 360. Once the housing 340 is positioned relative to the fastener 316, the spacer 360 is rotated relative to the housing 340 to align part cylindrical surfaces 364 or part cylindrical surfaces 365 with the passage 342 in the housing 340. The rod is placed into the passage 342 in The housing 340 and in engagement with the spacer 360. The set screw is threaded into the housing 340 and into engagement with the rod. The set screw clamps the rod, the spacer 360, and the housing 340 to the fastener 316 to prevent movement of the fastener relative to the housing. Alternatively, the fastener 316 may be connected to the vertebra prior to the spacer 360 and the spring member being inserted into the housing 340.

An apparatus 410 constructed according to another embodiment of the present invention is illustrated in FIGS. 12 and 12A. The apparatus 410 is substantially similar to the apparatus 10 illustrated in FIGS. 1–6. Accordingly, the apparatus 410 will not be described in detail.

The apparatus 410 includes a fastener 416 (FIG. 12) for connecting a surgically implantable longitudinal member or rod (not shown) to bone portions, such as vertebrae of a spinal column, to maintain the vertebrae in a desired spatial relationship. The rod and the fastener 416 are identical to the rod 12 and the fastener 16 illustrated in FIGS. 1–4. Accordingly, the rod and the fastener 416 will not be described in detail.

The fastener 416 extends into a housing 440 that interconnects the rod and the fastener. The housing 440 is identical to the housing illustrated in FIGS. 1–4. Accordingly, the housing 440 will not be described in detail. A part spherical surface of the fastener 416 engages a concave part spherical surface of the housing 440 so that the fastener is universally pivotable relative to the housing and an axis of the fastener is positionable in any one of a plurality of angular positions relative to an axis of a passage 444 of the housing.

A spacer 460 (FIGS. 12 and 12A) is housed in the passage 444 of the housing 440. The spacer 460 has a concave part spherical surface 462 that engages a part spherical surface of the fastener 416. The spacer 460 includes a planar upper surface 464 that engages the rod. The spacer 460 also has an opening 466 through which a tool (not shown) extends to engage a recess 432 in the fastener 416. The tool extends through the opening 466 to apply torque to the fastener 416 and connect the fastener to the vertebra.

The spacer 460 (FIG. 12A) has a circumferential groove 468 for receiving a compressible member such as a spring member (not shown). The housing 440 includes a circumferential groove (not shown) for receiving the spring member so that the spring member extends from the groove 468 in the spacer 460 to the groove in the housing. The spring member is identical to the spring member 70 illustrated in FIGS. 1–6.

When the spring member is received in the groove 468 in the spacer 460 and the groove in the housing 440, the spring member applies an axial force to the spacer 460 to prevent relative movement between the fastener 416 and the housing 440 when the rod is disengaged from the spacer and the spacer engages the fastener. The spring member urges the spacer 460 axially toward the fastener 416 so that the part spherical surface 462 of the spacer frictionally engages a part spherical surface of the fastener and another part spherical surface of the fastener frictionally engages the concave part spherical surface of the housing 440. The fastener 416 and the housing 440 are manually movable relative to each other by a surgeon when the rod is disengaged from the spacer 460 and the spring member applies the axial force. The force applied by the spring member may be overcome by the surgeon to move the housing 440 relative to the fastener 416. Accordingly, the housing 440 can be positioned relative to the fastener 416 and held in position relative to the fastener by the spring member without the rod engaging the spacer 460.

The spacer 460 has four axially extending slots 486. The slots 486 intersect the groove 468. A tool (not shown) has four prongs that extend through the slots 486 and into engagement with the spring member. The tool grasps the spacer 460 and the spring member for inserting the spacer and the spring member into the housing 440. The prongs of the tool engage the spring member to radially contract the spring member into the groove 468 in the spacer 460. The prongs hold the spring member in the radially contracted condition in the groove 468 while the spacer 460 and spring member are being inserted into the housing 440. Once the spacer 460 engages the fastener 416, the prongs are removed from the slots 486 and the spring member radially expands into the groove in the housing 440. Although the spacer 460 is described as having four slots 486, the spacer could have any number of slots and the tool would have the same number of prongs as the spacer has slots.

A clamping mechanism or set screw (not shown) threadably engages the housing 440. The clamping mechanism is identical to the clamping mechanism 90 illustrated in FIGS. 1–4. The set screw engages and applies a force to the rod to press the rod against the spacer 460 and the spacer against the fastener 416. The set screw clamps the rod, the spacer 460, and the housing 440 to the fastener 416 to prevent movement of the fastener relative to the housing. The force applied by the set screw cannot be overcome by the surgeon to move the housing 440 relative to the fastener 416.

The apparatus 410 is assembled by inserting the fastener 416 through the opening in the housing 440 so that a part spherical surface of the fastener engages a part spherical surface of the housing. The spacer 460 and the spring member are inserted into the housing 440 by radially compressing the spring member into the groove 468 in the spacer. The spacer 460 and the spring member are inserted into the passage 444 in the housing 440 until the part spherical surface 462 of the spacer engages a part spherical surface of the fastener 416. The spring member is released and expands radially into the groove in the housing 440.

A tool is inserted through the opening 466 in the spacer 460 and into the recess 432 in the fastener 416. Torque is applied to the fastener 416 to turn a thread convolution 424 into the vertebra. Once the fastener 416 is connected with the vertebra, the housing 440 can be positioned relative to the fastener. The spring member maintains the position of the housing 440 relative to the fastener 416 while the rod is disengaged from the spacer 460. Once the housing 440 is positioned relative to the fastener 416, the rod is placed into a passage 442 in the housing 440 and in engagement with the surface 464 of the spacer 460. The set screw is threaded into the housing 440 and into engagement with the rod. The set screw clamps the rod, the spacer 460, and the housing 440 to the fastener 416 to prevent movement of the fastener relative to the housing. Alternatively, the fastener 416 may be connected to the vertebra prior to the spacer 460 and the spring member being inserted into the housing 440.

Figure 15:
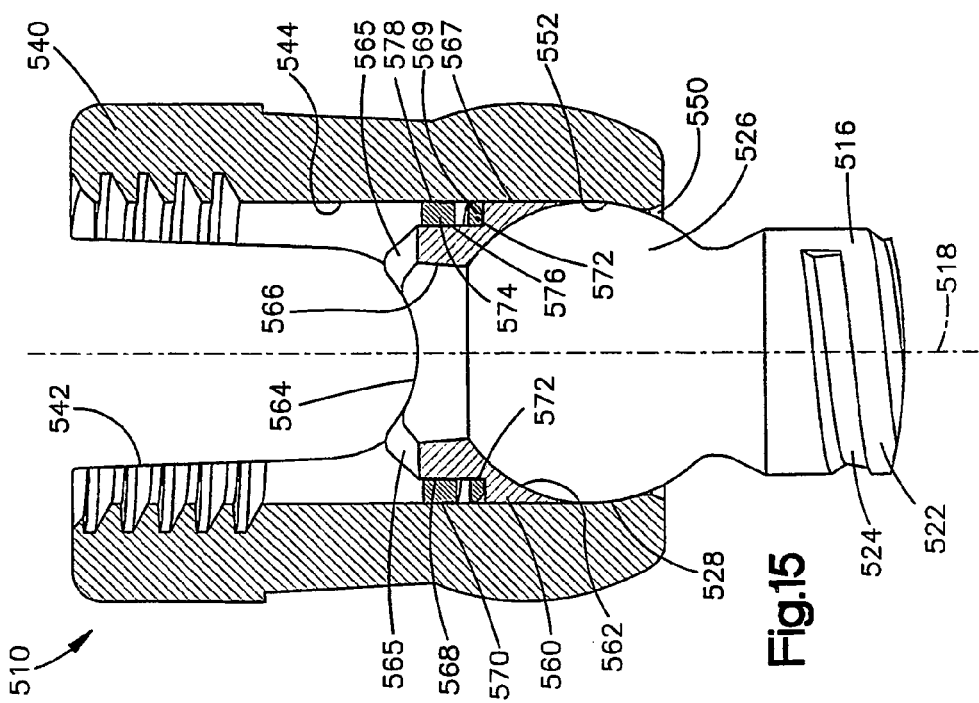
FIG. 15 is a sectional view of the apparatus of FIG. 13.

An apparatus 510 constructed according to another embodiment of the present invention is illustrated in FIGS. 13–15. The apparatus 510 includes a fastener 516 for connecting a surgically implantable longitudinal member or rod (not shown) to bone portions, such as vertebrae of a spinal column, to maintain the vertebrae in a desired spatial relationship. The fastener 516 has a longitudinal axis 518 and a threaded end portion 522 having a course thread convolution 524 which engages the vertebra. A second end portion 526 of the fastener 516 is provided with a spherical surface 528. A recess 532 is provided on the end portion 526 of the fastener 516. The recess 532 receives a tool (not shown) that applies torque to the fastener 516 to turn the thread convolution 524 into the vertebra.

The fastener 516 extends into a housing 540 that interconnects the rod and the fastener 516. The housing 540 has a first passage 542 through which the rod extends. The housing 540 has a second passage 544 with a longitudinal axis that extends transverse to the passage 542. The fastener 516 extends through an opening 550 in the housing 540 and into the second passage 544. The spherical surface 528 of the fastener 516 engages a concave part spherical surface 552 of the housing 540. Accordingly, the fastener 516 is universally pivotable relative to the housing 540 so that the longitudinal axis 518 of the fastener 516 is positionable in any one of a plurality of angular positions relative to the longitudinal axis of the passage 544.

A spacer 560 is housed in the second passage 544 of the housing 540. The spacer 560 (FIG. 15) has a concave part spherical surface 562 that engages the spherical surface 528 of the fastener 516. The spacer 560 (FIG. 14) has diametrically opposed concave part cylindrical surfaces 564. The surfaces 564 engage the rod when the surfaces 564 are aligned with the passage 542 in the housing 540. The spacer 560 also includes diametrically opposed concave part cylindrical surfaces 565. The surfaces 565 engage the rod when the surfaces 565 are aligned with the passage 542. The surfaces 564 are located at 90° relative to the surfaces 565. The spacer 560 has an opening 566 through which the tool (not shown) extends to engage the recess 532 in the fastener 516. The tool extends through the opening 566 to apply torque to the fastener 516 and connect the fastener to the vertebra.

The spacer 560 (FIGS. 14–15) has a first radially outer cylindrical surface 567 with an outer diameter slightly smaller than the diameter of the passage 544 in the housing 540. The spacer 560 includes a second radially outer cylindrical surface 568 having a diameter smaller than the cylindrical surface 567. A radially extending surface 569 extends from the cylindrical surface 568 to the cylindrical surface 567.

A ring-shaped retaining or positioning member 570 holds the spacer 560 in the housing 540. The retaining member 570 includes a plurality of spring members or leaf springs 572 extending from a retaining portion 574. The spring members 572 and the retaining portion 574 may be formed as a single, integral component. The spring members 572 may be formed by spirally cutting the retaining member. It is contemplated that the spring members 572 could be formed as separate pieces that are attached to the retaining portion 574. It is contemplated that the retaining member 570 may be made of any suitable biocompatible material such as an titanium-aluminum-vanadium alloy or a nickel-titanium alloy such as super-elastic Nitinol.

The spring members 572 engage the radially extending surface 569 on the spacer 560 to apply an axial force to the spacer to prevent relative movement between the fastener 516 and the housing 540 when the rod is disengaged from the spacer and the spacer engages the fastener. The spring members 572 urge the spacer 560 axially toward the fastener 516 and the part spherical surface 552 of the housing 540 against the spherical surface 528 of the fastener. The part spherical surface 562 of the spacer 560 frictionally engages the spherical surface 528 of the fastener 516 and the spherical surface 528 of the fastener frictionally engages the part spherical surface 552 of the housing 540. The fastener 516 and the housing 540 are manually movable relative to each other by a surgeon when the rod is disengaged from the spacer 560 and the spring members 572 apply the axial force. The force applied by the spring members 572 may be overcome by the surgeon to move the housing 540 relative to the fastener 516. Accordingly, the housing 540 can be positioned relative to the fastener 516 and held in position relative to the fastener by the spring members 572 without the rod engaging the spacer 560.

The retaining portion 574 (FIG. 15) of the retaining member 570 has a radially inner cylindrical surface 576 with a diameter slightly larger than the outside diameter of the cylindrical surface 568 on the spacer 560. The retaining portion 574 of the retaining member 570 has a radially outer cylindrical surface 578 that engages the housing 540. The retaining portion 574 of the retaining member 570 is press-fit into the passage 544 in the housing 540 to fixedly connect the retaining member to the housing 540.

The spring members 572 have an outer diameter that is smaller than the diameter of the passage 544 in the housing 540. Accordingly, the spring members 572 can move relative to the housing 540. The spacer 560 can move axially relative to the housing 540 and the retaining portion 574 when the rod is disengaged from the spacer 560.

The amount of axial force applied by the spring members 572 to the spacer 560 depends on the position of the retaining portion 574 relative to the housing 540 and the spacer 560. The retaining portion 574 may be press-fit into the housing 540 in any one of a plurality of axial positions relative to the housing. It is contemplated that the retaining portion 574 may be connected to the housing 540 in a desired manner. Accordingly, the amount of axial force applied by the spring members 572 to the spacer 560 may be adjusted to a desired force. The force applied by the spring members 572 increases as the retaining portion 574 gets closer to the radial surface 569 on the spacer 560.

A clamping mechanism or set screw (not shown) threadably engages the housing 540. The set screw engages and applies a force to the rod to press the rod against the spacer 560 and the spacer against the fastener 516. The set screw clamps the rod, the spacer 560, and the housing 540 to the fastener 516 to prevent movement of the fastener relative to the housing. The force applied by the set screw cannot be overcome by the surgeon to move the housing 540 relative to the fastener 516.

The apparatus 510 is assembled by inserting the fastener 516 through the opening 550 in the housing 540 so that the spherical surface 528 of the fastener engages the part spherical surface 552 of the housing. The spacer 560 is inserted into the housing 540 and into engagement with the fastener 516. The retaining member 570 is inserted into the second passage 544 until the spring members 572 engage the spacer 560 and the spring members apply the desired force to the spacer 560.

A tool is inserted through the opening 566 in the spacer 560 and into the recess 532 in the fastener 516. Torque is applied to the fastener 516 to turn the thread convolution 524 into the vertebra. Once the fastener 516 is connected with the vertebra, the housing 540 can be positioned relative to the fastener. The spring members 572 maintain the position of the housing 540 relative to the fastener 516 while the rod is disengaged from the spacer 560. Once the housing 540 is positioned relative to the fastener 516, the spacer 560 is rotated relative to the housing 540 to align the surfaces 564 or 565 with the passage 542 in the housing. The rod is placed into the passage 542 and in engagement with the spacer 560. The set screw is threaded into the housing 540 and into engagement with the rod. The set screw clamps the rod, the spacer 560, and the housing 540 to the fastener 516 to prevent movement of the fastener relative to the housing. Alternatively, the fastener 516 may be connected to the vertebra prior to the spacer 560 and the retaining member 570 being inserted into the housing 540.

Figure 16:
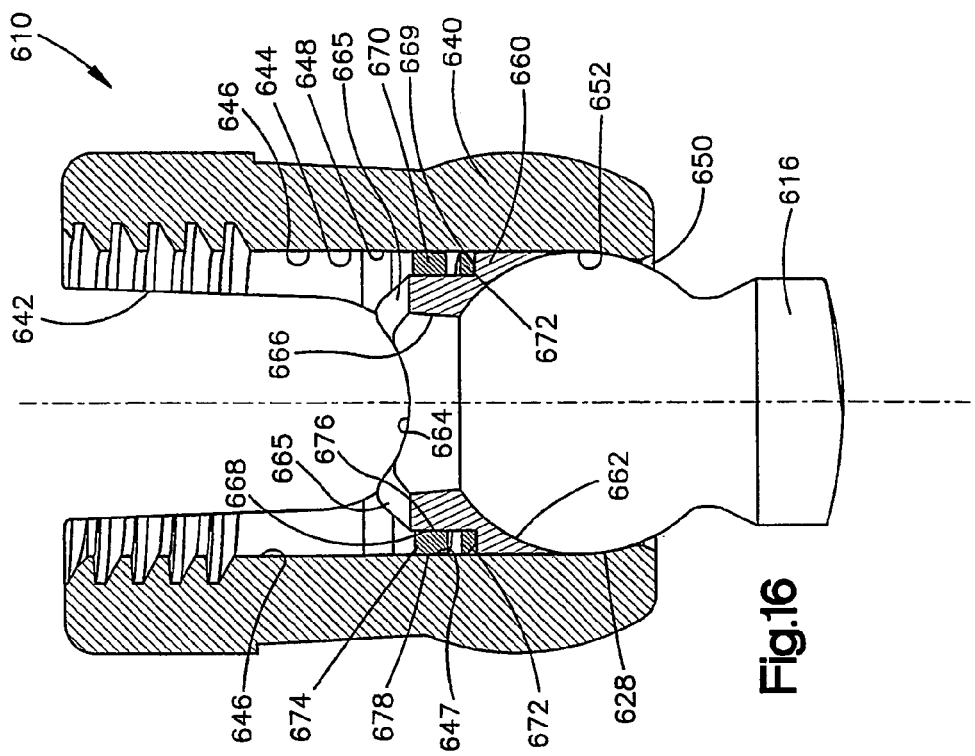
FIG. 16 is a sectional view of an apparatus constructed in accordance with another embodiment of the present invention with portions removed for clarity.

An apparatus 610 constructed according to another embodiment of the present invention is illustrated in FIG. 16. The apparatus 610 is substantially similar to the apparatus 510 illustrated in FIGS. 13–15. Accordingly, the apparatus 610 will not be described in detail.

The apparatus 610 includes a fastener 616 for connecting a surgically implantable longitudinal member or rod (not shown) to bone portions, such as vertebrae of a spinal column, to maintain the vertebrae in a desired spatial relationship. The fastener 616 is identical to the fastener 516 illustrated in FIGS. 13–15. Accordingly, the fastener 616 will not be described in detail.

The fastener 616 extends into a housing 640 that interconnects the rod and the fastener 616. The housing 640 has a first passage 642 through which the rod extends. The housing 640 has a second passage 644 that extends transverse to the passage 642. The passage 644 is defined by a pair of first or upper part cylindrical surfaces 646 having a first diameter. The housing 640 has a second or lower cylindrical surface 647 having a second diameter smaller than the first diameter. A tapered surface 648 extends from the first cylindrical surfaces 646 to the second cylindrical surface 648.

The fastener 616 extends through an opening 650 in the housing 640 and into the second passage 644. A spherical surface 628 of the fastener 616 engages a concave part spherical surface 652 of the housing 640. Accordingly, the fastener 616 is universally pivotable relative to the housing 640 so that a longitudinal axis of the fastener 616 is positionable in any one of a plurality of angular positions relative to a longitudinal axis of the passage 644.

A spacer 660 is housed in the second passage 644 of the housing 640. The spacer 660 is identical to the spacer 560 illustrated in FIGS. 13–14. Accordingly, the spacer 660 will not be described in detail.

A ring-shaped retaining member 670 holds the spacer 660 in the housing 640. The retaining member 670 is identical to the retaining member 570 illustrated in FIGS. 14–15. Accordingly, the retaining member 670 will not be described in detail. The retaining member 670 includes spring members 672. The spring members 672 engage a radially extending surface 669 on the spacer 660 to apply an axial force to the spacer to prevent relative movement between the fastener 616 and the housing 640 when the rod is disengaged from the spacer and the spacer engages the fastener. The spring members 672 urge the spacer 660 axially toward the fastener 616 and the part spherical surface 652 of the housing 640 against the spherical surface 628 of the fastener.

A part spherical surface 662 of the spacer 660 frictionally engages the spherical surface 628 of the fastener 616 and the spherical surface 628 of the fastener frictionally engages the part spherical surface 652 of the housing 640. The fastener 616 and the housing 640 are manually movable relative to each other by a surgeon when the rod is disengaged from the spacer 660 and the spring members 672 apply the axial force. The force applied by the spring members 672 may be overcome by the surgeon to move the housing 640 relative to the fastener 616. Accordingly, the housing 640 can be positioned relative to the fastener 616 and held in position relative to the fastener by the spring members 672 without the rod engaging the spacer 660.

A retaining portion 674 of the retaining member 670 has a radially inner cylindrical surface 676 with a diameter slightly larger than the outside diameter of a radially outer cylindrical surface 668 on the spacer 660. The retaining portion 674 has a radially outer cylindrical surface 678 that engages the housing 640. The outer cylindrical surface 678 has a diameter which is slightly smaller than the diameter of the cylindrical surfaces 646 of the housing 640 and slightly larger than the diameter of the cylindrical surface 647 of the housing. Accordingly, the retaining member 670 is easily inserted into the housing 640. The retaining portion 674 engages the tapered surface 648 of the housing 640. The retaining portion 674 is then press-fit into engagement with the surface 647 of the housing 640 to fixedly connect the retaining member 670 to the housing.

The spring members 672 have an outer diameter that is smaller than the diameter of the cylindrical surface 647 of the housing 640. Accordingly, the spring members 672 can move relative to the housing 640. The spacer 660 can move axially relative to the housing 640 and the retaining portion 674 when the rod is disengaged from the spacer 660.

The amount of axial force applied by the spring members 672 to the spacer 660 depends on the position of the retaining portion 674 relative to the housing 640 and the spacer 660. The retaining portion 674 may be press-fit into the housing 640 in any one of a plurality of axial positions relative to the housing. Accordingly, the amount of axial force applied by the spring members 672 to the spacer 660 may be adjusted to a desired force.

A clamping mechanism or set screw (not shown) threadably engages the housing 640. The set screw engages and applies a force to the rod to press the rod against the spacer 660 and the spacer against the fastener 616. The set screw clamps the rod, the spacer 660, and the housing 640 to the fastener 616 to prevent movement of the fastener relative to the housing. The force applied by the set screw cannot be overcome by the surgeon to move the housing 640 relative to the fastener 616.

The apparatus 610 is assembled by inserting the fastener 616 through the opening 650 in the housing 640 so that the spherical surface 628 of the fastener engages the part spherical surface 652 of the housing. The spacer 660 is inserted into the housing 640 and into engagement with the fastener 616. The retaining member 670 is inserted into the second passage 644 until the retaining portion 674 engages the surface 647 of the housing and the spring members 672 engage the spacer 660. The retaining member 670 is inserted into the housing 640 so that the spring members 672 apply the desired force to the spacer 660.

A tool is inserted through an opening 666 in the spacer 660 and into a recess in the fastener 616. Torque is applied to the fastener 616 to thread the fastener into the vertebra. Once the fastener 616 is connected with the vertebra, the housing 640 can be positioned relative to the fastener. The spring members 672 maintain the position of the housing 640 relative to the fastener 616 while the rod is disengaged from the spacer 660. Once the housing 640 is positioned relative to the fastener 616, the spacer 660 is rotated relative to the housing to align part cylindrical surfaces 664 or 665 with the passage 642 in the housing. The rod is placed into the passage 642 and in engagement with the spacer 660. The set screw is threaded into the housing 640 and into engagement with the rod. The set screw clamps the rod, the spacer 660, and the housing 640 to the fastener 616 to prevent movement of the fastener relative to the housing. Alternatively, the fastener 616 may be connected to the vertebra prior to the spacer 660 and the retaining member 670 being inserted into the housing 640.

Figure 18:
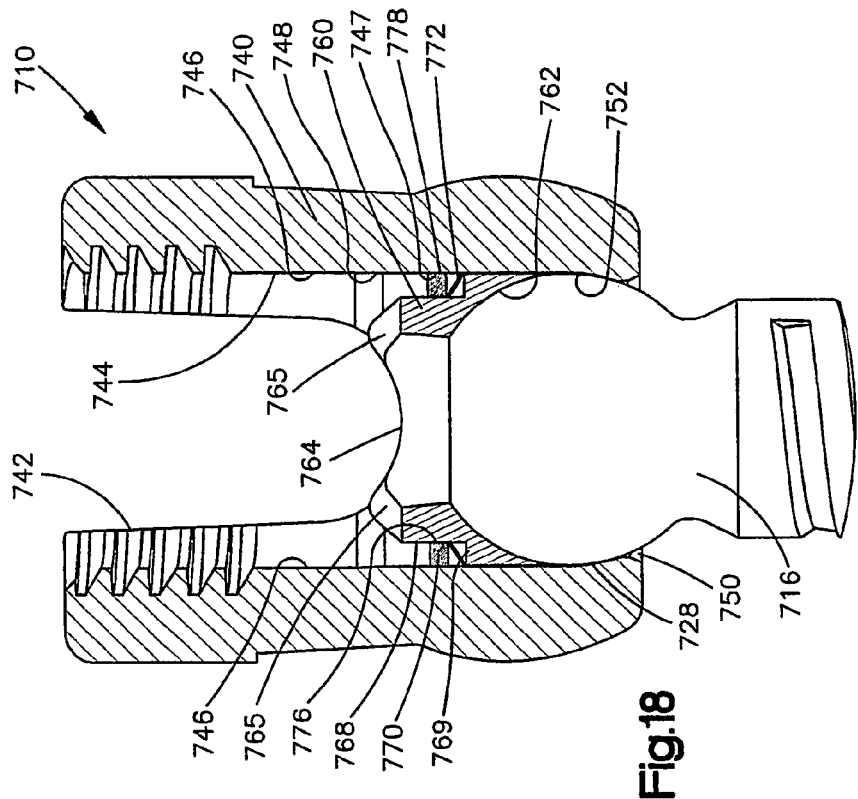
FIG. 18 is a sectional view of the apparatus of FIG. 17.
Figure 17:
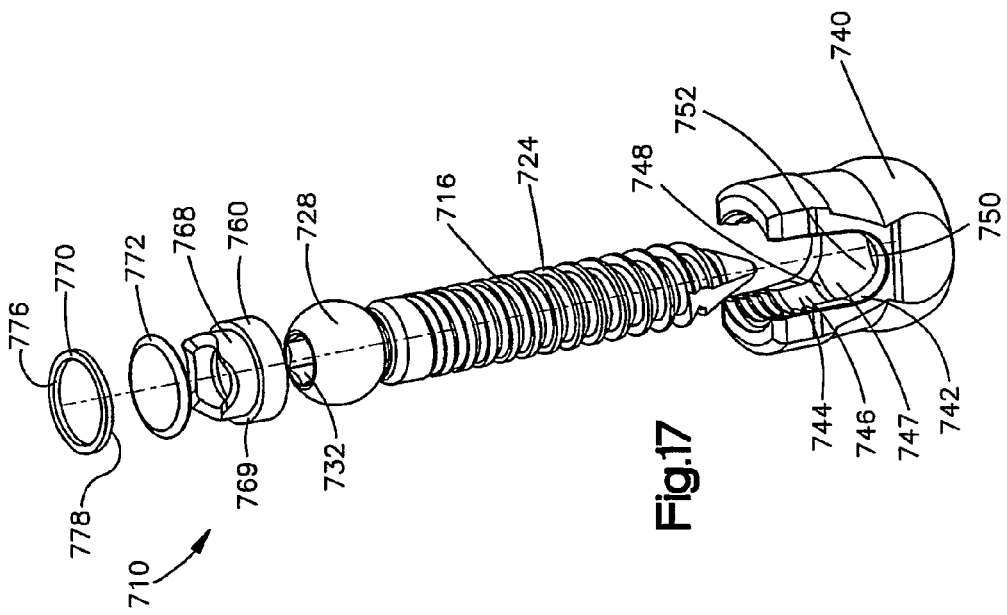
FIG. 17 is an exploded view of an apparatus constructed in accordance with another embodiment of the present invention.

An apparatus 710 constructed according to another embodiment of the present invention is illustrated in FIGS. 17–18. The apparatus 710 is substantially similar to the apparatus 610 illustrated in FIG. 16. Accordingly, the apparatus 710 will not be described in detail.

The apparatus 710 includes a fastener 716 for connecting a surgically implantable longitudinal member or rod (not shown) to bone portions, such as vertebrae of a spinal column, to maintain the vertebrae in a desired spatial relationship. The fastener 716 is identical to the fastener 616 illustrated in FIG. 16. Accordingly, the fastener 716 will not be described in detail.

The fastener 716 extends into a housing 740 that interconnects the rod and the fastener 716. The housing 740 is identical to the housing 640 illustrated in FIG. 16. Accordingly, the housing 740 will not be described in detail. A spherical surface 728 of the fastener 716 engages a concave part spherical surface 752 of the housing 740. Accordingly, the fastener 716 is universally pivotable relative to the housing 740 so that a longitudinal axis of the fastener 716 is positionable in any one of a plurality of angular positions relative to a longitudinal axis of a passage 744 of the housing 740.

A spacer 760 is housed in the passage 744 of the housing 740. The spacer 760 is identical to the spacer 660 illustrated in FIG. 16. Accordingly, the spacer 760 will not be described in detail.

A ring-shaped retaining member 770 holds the spacer 760 in the housing 740. A Bellville washer or spring member 772 engages the retainer member 770 and the spacer 760. It is contemplated that the spring member 772 may have any desired shape. The spring member 772 engages a radially extending surface 769 on the spacer 760 to apply an axial force to the spacer to prevent relative movement between the fastener 716 and the housing 740 when the rod is disengaged from the spacer and the spacer engages the fastener. The spring member 772 urges the spacer 760 axially toward the fastener 716 and the part spherical surface 752 of the housing 740 against the spherical surface 728 of the fastener. A part spherical surface 762 of the spacer 760 frictionally engages the spherical surface 728 of the fastener 716 and the spherical surface 728 of the fastener frictionally engages the part spherical surface 752 of the housing 740. The fastener 716 and the housing 740 are manually movable relative to each other by a surgeon when the rod is disengaged from the spacer 760 and the spring member 772 applies the axial force. The force applied by the spring member 772 may be overcome by the surgeon to move the housing 740 relative to the fastener 716. Accordingly, the housing 740 can be positioned relative to the fastener 716 and held in position relative to the fastener by the spring member 772 without the rod engaging the spacer 760.

The retaining member 770 has a radially inner cylindrical surface 776 with a diameter slightly larger than the outside diameter of a radially outer cylindrical surface 768 on the spacer 760. The retaining member 770 has a radially outer cylindrical surface 778 with a diameter slightly smaller than the diameter of cylindrical surfaces 746 of the housing 740. The diameter of the outer cylindrical surface 778 of the retaining member 770 is slightly smaller than the diameter of cylindrical surface 747 of the housing 740. Accordingly, the retaining member 770 is easily inserted into the housing 740. The retaining member 770 engages a tapered surface 748 of the housing 740. The retaining member 770 is press-fit into the housing 740 in engagement with the surface 747 to fixedly connect the retaining member to the housing 740. The spacer 760 can move axially relative to the housing 740 and the retaining member 770 when the rod is disengaged from the spacer 760.

The amount of axial force applied by the spring member 772 to the spacer 760 depends on the position of the retaining member 770 relative to the housing 740 and the spacer 760. The retaining member 770 may be press-fit into the housing 740 in any one of a plurality of axial positions relative to the housing. Accordingly, the amount of axial force applied by the spring member 772 to the spacer 760 may be adjusted to a desired force.

A clamping mechanism or set screw (not shown) threadably engages the housing 740. The set screw engages and applies a force to the rod to press the rod against the spacer 760 and the spacer against the fastener 716. The set screw clamps the rod, the spacer 760, and the housing 740 the fastener 716 to prevent movement of the fastener relative to the housing. The force applied by the set screw cannot be overcome by the surgeon to move the housing 740 relative to the fastener 716.

The apparatus 710 is assembled by inserting the fastener 716 through an opening 750 in the housing 740 so that the spherical surface 728 of the fastener engages the part spherical surface 752 of the housing. The spacer 760 is inserted into the housing 740 and into engagement with the fastener 716. The spring member 772 is inserted into the second passage 744 until the retaining ring engages the surface 747 of the housing and the spacer 760. The retaining member 770 is inserted into the second passage 744 until the retaining member engages the surface 747 of the housing and the spring member 772. The retaining member 770 is inserted into the housing 740 so that the spring member 772 applies the desired force to the spacer 760.

A tool is inserted through an opening 766 in the spacer 760 and into a recess 732 in the fastener 716. Torque is applied to the fastener 716 to turn a thread convolution 724 into the vertebra. Once the fastener 716 is connected with the vertebra, the housing 740 can be positioned relative to the fastener. The spring member 772 maintains the position of the housing 740 relative to the fastener 716 while the rod is disengaged from the spacer 760. Once the housing 740 is positioned relative to the fastener 716, the spacer 760 is rotated so that part cylindrical surfaces 764 or 765 are aligned with a passage 742 in the housing. The rod is placed into the passage 742 and in engagement with the spacer 760. The set screw is threaded into the housing 740 and into engagement with the rod. The set screw clamps the rod, the spacer 760, and the housing 740 to the fastener 716 to prevent movement of the fastener relative to the housing. Alternatively, the fastener 716 may be connected to the vertebra prior to the spacer 760 and the retaining member 770 being inserted into the housing 740.

An apparatus 810 constructed according to another embodiment of the present invention is illustrated in FIG. 19. The apparatus 810 is substantially similar to the apparatus 610 illustrated in FIG. 16. Accordingly, the apparatus 810 will not be described in detail.

The apparatus 810 includes a fastener 816 for connecting a surgically implantable longitudinal member or rod (not shown) to bone portions, such as vertebrae of a spinal column, to maintain the vertebrae in a desired spatial relationship. The fastener 816 is identical to the fastener 616 illustrated in FIG. 16. Accordingly, the fastener 816 will not be described in detail.

The fastener 816 extends into a housing 840 that interconnects the rod and the fastener 816. The housing 840 is substantially similar to the housing 640 illustrated in FIG. 16. Accordingly, the housing 840 will not be described in detail. A spherical surface 828 of the fastener 816 engages a concave part spherical surface 852 of the housing 840. Accordingly, the fastener 816 is universally pivotable relative to the housing 840 so that a longitudinal axis of the fastener 816 is positionable in any one of a plurality of angular positions relative to a longitudinal axis of a passage 844 of the housing 840.

The housing 840 includes two diametrically opposed openings 854. The openings 854 are defined by deformable radially inner walls 856. The walls 856 are deformed radially inwardly after insertion of the fastener 816 to help retain the fastener in the housing 840.

A spacer 860 is housed in the passage 844 of the housing 840. The spacer 860 is identical to the spacer 660 illustrated in FIG. 16. Accordingly, the spacer 860 will not be described in detail.

A ring-shaped retaining member 870 holds the spacer 860 in the housing 840. The retaining member 870 is identical to the retaining member 670 illustrated in FIG. 16. Accordingly, the retaining member 870 will not be described in detail. The retaining member 870 includes spring members 872. The spring members 872 engage a radially extending surface 869 on the spacer 860 to apply an axial force to the spacer to prevent relative movement between the fastener 816 and the housing 840 when the rod is disengaged from the spacer and the spacer engages the fastener. The spring members 872 urge the spacer 860 axially toward the fastener 816 and the part spherical surface 852 of the housing 840 against the spherical surface 828 of the fastener. A part spherical surface 862 of the spacer 860 frictionally engages the spherical surface 828 of the fastener 816 and the spherical surface 828 of the fastener frictionally engages the part spherical surface 852 of the housing 840. The fastener 816 and the housing 840 are manually movable relative to each other by a surgeon when the rod is disengaged from the spacer 860 and the spring members 872 apply the axial force. The force applied by the spring members 872 may be overcome by the surgeon to move the housing 840 relative to the fastener 816. Accordingly, the housing 840 can be positioned relative to the fastener 816 and held in position relative to the fastener by the spring members 872 without the rod engaging the spacer 860.

A retaining portion 874 of the retaining member 870 has a radially inner cylindrical surface 876 with a diameter slightly larger than the outside diameter of a radially outer cylindrical surface 868 on the spacer 860. The retaining portion 874 has a radially outer cylindrical surface 878 that engages the housing 840. The outer cylindrical surface 878 has a diameter which is slightly smaller than the diameter of first or upper cylindrical surfaces 846 of the housing 840 and slightly larger than the diameter of second or lower cylindrical surface 847 of the housing. Accordingly, the retaining member 870 is easily inserted into the housing 840. The retaining portion 874 engages a tapered surface 848 of the housing 840. The retaining portion 874 is then press-fit into engagement with the surface 847 of the housing 840.

The spring members 872 have an outer diameter that is smaller than the diameter of the surface 847 of the housing 840. Accordingly, the spring members 872 can move relative to the housing 840. The spacer 860 can move axially relative to the housing 840 and the retaining portion 874 when the rod is disengaged from the spacer.

The amount of axial force applied by the spring members 872 to the spacer 860 depends on the position of the retaining portion 874 relative to the housing 840 and the spacer 860. The retaining portion 874 may be press-fit into the housing 840 in any one of a plurality of axial positions relative to the housing. Accordingly, the amount of axial force applied by the spring members 872 to the spacer 860 may be adjusted to a desired force.

A clamping mechanism or set screw (not shown) threadably engages the housing 840. The set screw engages and applies a force to the rod to press the rod against the spacer 860 and the spacer against the fastener 816. The set screw clamps the rod, the spacer 860, and the housing 840 to the fastener 816 to prevent movement of the fastener relative to the housing. The force applied by the set screw cannot be overcome by the surgeon to move the housing 840 relative to the fastener 816.

The apparatus 810 is assembled by inserting the fastener 816 through an opening 850 in the housing 840 so that the spherical surface 828 of the fastener engages the part spherical surface 852 of the housing. The spacer 860 is inserted into the housing 840 and into engagement with the fastener 816. The retaining member 870 is inserted into the passage 844 until the retaining portion 874 engages the surface 847 of the housing and the spring members 872 engage the spacer 860. The retaining member 870 is inserted into the housing 840 so that the spring members 872 apply the desired force to the spacer 860.

A tool is inserted through an opening 866 in the spacer 860 and into a recess in the fastener 816. Torque is applied to the fastener 816 to turn a thread convolution 824 into the vertebra. Once the fastener 816 is connected with the vertebra, the housing 840 can be positioned relative to the fastener. The spring members 872 maintain the position of the housing 840 relative to the fastener. 816 while the rod is disengaged from the spacer 860. Once the housing 840 is positioned relative to the fastener 816, the spacer 860 is rotated so that part cylindrical surfaces 864 or 865 are aligned with a passage 842 in the housing. The walls 856 of the housing 840 are deformed radially inward to the position shown in FIG. 19. Accordingly, the walls 856 help retain the retaining member 870, the spacer 860, and the fastener 816 in the housing 840. The rod is placed into the passage 842 and in engagement with the spacer 860. The set screw is threaded into the housing 840 and into engagement with the rod. The set screw clamps the rod, the spacer 860, and the housing 840 to the fastener 816 to prevent movement of the fastener relative to the housing. Alternatively, the fastener 816 may be connected to the vertebra prior to the spacer 860 and the retaining member 870 being inserted into the housing 840.

Figure 21:
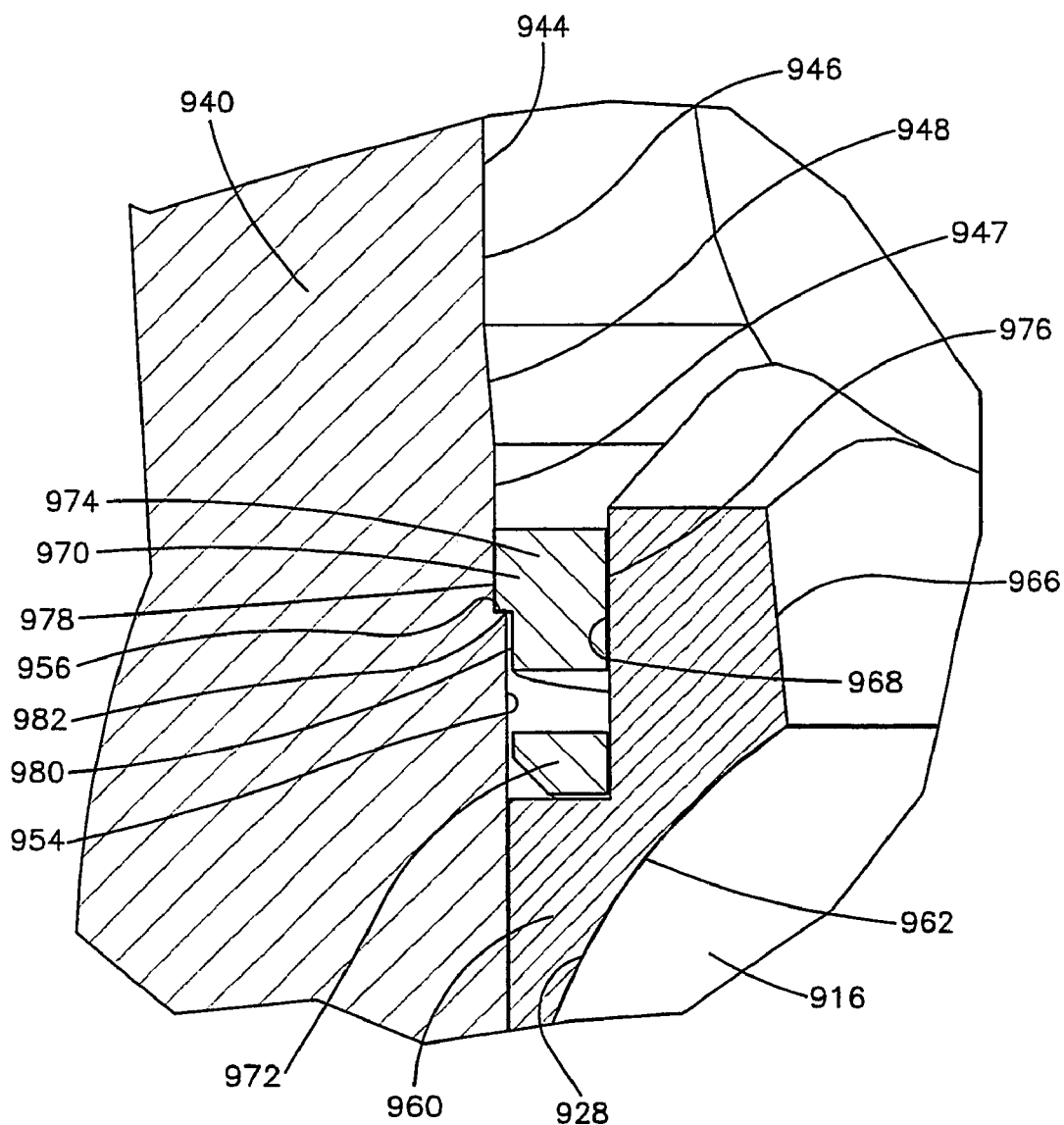
FIG. 21 is an enlarged sectional view of a portion of the apparatus of FIG. 20.

An apparatus 910 constructed according to another embodiment of the present invention is illustrated in FIGS. 20–21. The apparatus 910 is substantially similar to the apparatus 610 illustrated in FIGS. 16. Accordingly, the apparatus 910 will not be described in detail.

The apparatus 910 includes a fastener 916 for connecting a surgically implantable longitudinal member or rod (not shown) to bone portions, such as vertebrae of a spinal column, to maintain the vertebrae in a desired spatial relationship. The fastener 916 is identical to the fastener 616 illustrated in FIG. 16. Accordingly, the fastener 916 will not be described in detail.

The fastener 916 extends into a housing 940 that interconnects the rod and the fastener 916. The housing 940 is substantially similar to the housing 640 illustrated in FIG. 16. Accordingly, the housing 940 will not be described in detail. A spherical surface 928 of the fastener 916 engages a concave part spherical surface 952 of the housing 940. Accordingly, the fastener 916 is universally pivotable relative to the housing 940 so that a longitudinal axis of the fastener 916 is positionable in any one of a plurality of angular positions relative to a longitudinal axis of a passage 944 of the housing 940.

The housing 940 (FIG. 2-1) includes a lower cylindrical surface 954 with a diameter smaller than the diameter of an intermediate cylindrical surface 947. A radially extending surface 956 extends from the cylindrical surface 947 to the cylindrical surface 954.

A spacer 960 (FIGS. 20–21) is housed in the passage 944 of the housing 940. The spacer 960 is identical to the spacer 660 illustrated in FIG. 16. Accordingly, the spacer 960 will not be described in detail.

A ring-shaped retaining member 970 holds the spacer 960 in the housing 940. The retaining member 970 is substantially similar to the retaining member 670 illustrated in FIG. 16. Accordingly, the retaining member 970 will not be described in detail. The retaining member 970 includes spring members 972. The spring members 972 engage a radially extending surface 969 on the spacer 960 to apply an axial force to the spacer to prevent relative movement between the fastener 916 and the housing 940 when the rod is disengaged from the spacer and the spacer engages the fastener. The spring members 972 urge the spacer 960 axially toward the fastener 916 and the part spherical surface 952 of the housing 940 against the spherical surface 928 of the fastener. A part spherical surface 962 of the spacer 960 frictionally engages the spherical surface 928 of the fastener 916 and the spherical surface 928 of the fastener frictionally engages the part spherical surface 952 of the housing 940. The fastener 916 and the housing 940 are manually movable relative to each other by a surgeon when the rod is disengaged from the spacer 960 and the spring members 972 apply the axial force. The force applied by the spring members 972 may be overcome by the surgeon to move the housing 940 relative to the fastener 916. Accordingly, the housing 940 can be positioned relative to the fastener 916 and held in position relative to the fastener by the spring members 972 without the rod engaging the spacer 960.

A retaining portion 974 of the retaining member 970 has a radially inner cylindrical surface 976 with a diameter slightly larger than the outside diameter of a radially outer cylindrical surface 968 on the spacer 960. The retaining portion 974 has a radially outer cylindrical surface 978 that engages the housing 940. The outer cylindrical surface 978 has a diameter which is slightly smaller than the diameter of upper cylindrical surfaces 946 of the housing 940 and slightly larger than the diameter of the intermediate cylindrical surface 947 of the housing. Accordingly, the retaining member 970 is easily inserted into the housing 940. The retaining portion 974 engages a tapered surface 948 of the housing 940. The retaining portion 974 is then press-fit into engagement with the intermediate surface 947 of the housing 940 to fixedly connect the retaining member 970 to the housing.

The spring members 972 have an outer diameter that is smaller than the diameter of the lower cylindrical surface 954 of the housing 940. Accordingly, the spring members 972 can move relative to the housing 940. The spacer 960 can move axially relative to the housing 940 and the retaining portion 974 when the rod is disengaged from the spacer 960.

The amount of axial force applied by the spring members 972 to the spacer 960 depends on the position of the retaining portion 974 relative to the housing 940 and the spacer 960. The retaining portion 974 may be press-fit into the housing in any one of a plurality of axial positions relative to the housing. Accordingly, the amount of axial force applied by the spring members 972 to the spacer 960 may be adjusted to a desired force.

The retaining portion 974 (FIG. 21) includes another radially outer cylindrical surface 980 with a diameter less than the diameter of the lower cylindrical surface 954 of the housing 940. A radially extending surface 982 extends from the cylindrical surface 978 to the cylindrical surface 980. The radially extending surface 982 on the retaining portion 974 is engageable with the radially extending surface 956 on the housing 940. The radial surface 982 on the retaining portion 974 engages the radial surface 956 on the housing 940 to limit the distance that the retaining portion is inserted into the housing. Accordingly, the maximum force applied by the spring members 972 is limited.

A clamping mechanism or set screw (not shown) threadably engages the housing 940. The set screw engages and applies a force to the rod to press the rod against the spacer 960 and the spacer against the fastener 916. The set screw clamps the rod, the spacer 960, and the housing 940 to the fastener 916 to prevent movement of the fastener relative to the housing. The force applied by the set screw cannot be overcome by the surgeon to move the housing 940 relative to the fastener 916.

The apparatus 910 is assembled by inserting the fastener 916 through an opening 950 in the housing 940 so that the spherical surface 928 of the fastener engages the part spherical surface 952 of the housing. The spacer 960 is inserted into the housing 940 and into engagement with the fastener 916. The retaining member 970 is inserted into the second passage 944 until the retaining portion 974 engages the surface 947 of the housing and the spring members 972 engage the spacer 960 or the radially extending surface 982 engages the radially extending surface 956 on the housing. The retaining member 970 is inserted into the housing 940 so that the spring members 972 apply the desired axial force to the spacer 960. The surface 982 on the spacer 960 may not engage the surface 956 on the housing 940 when the spring members 972 apply the desired force to the spacer.

A tool is inserted through an opening 966 in the spacer 960 and into a recess 932 in the fastener 916. Torque is applied to the fastener 916 to turn a thread convolution into the vertebra. Once the fastener 916 is connected with the vertebra, the housing 940 can be positioned relative to the fastener. The spring members 972 maintain the position of the housing 940 relative to the fastener 916 while the rod is disengaged from the spacer 960. Once the housing 940 is positioned relative to the fastener 916, the spacer 960 is rotated so that part cylindrical surfaces 964 or 965 are aligned with a passage 942 in the housing. The rod is placed into the passage 942 and in engagement with the spacer 960. The set screw is threaded into the housing 940 and into engagement with the rod. The set screw clamps the rod, the spacer 960, and the housing 940 to the fastener 916 to prevent movement of the fastener relative to the housing. Alternatively, the fastener 916 may be connected to the vertebra prior to the spacer 960 and the retaining member 970 being inserted into the housing 940.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for connecting a longitudinal member with a bone portion, comprising:
   a fastener having a longitudinal axis and engageable with the bone portion;
   a housing having a passage with a first transverse dimension, said fastener extending through an opening in said housing into said passage and being movable relative to said housing, said longitudinal axis of said fastener being positionable in any one of a plurality of angular positions relative to a longitudinal axis of said passage;
   a spacer received in said passage of said housing and engageable with said fastener, the spacer having a radial surface having a transverse dimension smaller than said first transverse dimension of said passage in the housing;
   a retaining structure having a second transverse dimension greater than the first transverse dimension, the retaining structure being press-fit into the passage, the retaining structure and the passage being deformable relative to one another to adjust the distance between said retaining structure and the radial surface of the spacer; and
   a ring-shaped positioning member positioned between the retaining structure and the spacer, said positioning member configured to apply an adjustable force to the radial surface of the spacer to prevent relative movement between said fastener and said housing when said spacer engages said fastener, the force being adjustable by the distance between the retaining structure and the radial surface.

2. An apparatus as defined in claim 1 wherein said member is a compressible member.

3. An apparatus as defined in claim 1 wherein said member is a spring member.

4. An apparatus as defined in claim 1 wherein said fastener includes a first part spherical surface engageable with a part spherical surface of said housing.

5. An apparatus as defined in claim 4 wherein said fastener includes a second part spherical surface engageable with said spacer.

6. An apparatus as defined in claim 5 wherein said fastener, includes a surface engageable with said spacer to limit relative movement between said fastener and said housing.

7. An apparatus as defined in claim 6 wherein said second part spherical surface has a diameter smaller than a diameter of said first part spherical surface, said surface engageable with said spacer to limit relative movement between said fastener and said housing extending between said first and second part spherical surfaces.

8. An apparatus as defined in claim 1 wherein said spacer has an opening through which a tool can be extended to engage said fastener.

9. An apparatus as defined in claim 1 wherein said spacer includes slots that receive a tool for inserting said spacer into said housing.

10. An apparatus as defined in claim 1, further comprising a clamping mechanism and a longitudinal member, wherein said clamping mechanism includes a threaded member threadably engageable with said housing.

11. An apparatus as defined in claim 10 wherein said threaded member engages said longitudinal member to clamp said longitudinal member against said spacer.

12. An apparatus as defined in claim 10 wherein said threaded member and said housing have a buttress thread.

13. An apparatus as defined in claim 1 wherein said spacer includes a first pair of diametrically opposed part cylindrical surfaces engageable with said longitudinal member and a second pair of diametrically opposed part cylindrical surfaces engageable with said longitudinal member, said spacer being rotatable relative to said housing to align one of said first and second pair of diametrically opposed part cylindrical surfaces with said first passage in said housing.

14. An apparatus as defined in claim 1 wherein said spacer comprises a tab received in said first passage to engage a surface of said housing defining said first passage and to permit angular rotation of said spacer in said housing of at least about 100 and less than about 30°.

15. An apparatus for connecting a longitudinal member with a bone portion, comprising:
    a fastener having a longitudinal axis and engageable with the bone portion;
    a housing having a passage with a first transverse dimension, said fastener extending through an opening in said housing into said passage and being movable relative to said housing, said longitudinal axis of said fastener being positionable in any one of a plurality of angular positions relative to a longitudinal axis of said passage;
    a spacer received in said passage of said housing and engageable with said fastener, the spacer having a radial surface having a transverse dimension smaller than said first transverse dimension of said passage in the housing;
    a retaining structure having a second transverse dimension greater than the first transverse dimension, the retaining structure being press-fit into the passage, the retaining structure and the passage being deformable relative to one another to adjust the distance between said retaining structure and the radial surface of the spacer; and
    a positioning member positioned between the retaining structure and the spacer, said positioning member configured to apply an adjustable force to the radial surface of the spacer to prevent relative movement between said fastener and said housing when said spacer engages said fastener, the force being adjustable by the distance between the retaining structure and the radial surface;
wherein said housing includes a portion deformable to retain said member in said housing.

16. An apparatus comprising:
    a longitudinal member connectable with a bone portion;
    a fastener having a longitudinal axis and engageable with the bone portion to connect said longitudinal member to the bone portion;
    a housing having a first passage configured to receive said longitudinal member, said housing having a second passage with a longitudinal axis extending transverse to said first passage, said fastener extending through an opening in said housing into said second passage and being movable relative to said housing, said longitudinal axis of said fastener being positionable in any one of a plurality of angular positions relative to said longitudinal axis of said second passage;

a spacer received in said second passage of said housing and engageable with said fastener and said longitudinal member;

a positioning member that applies a force to prevent relative movement between said fastener and said housing when said longitudinal member is disengaged from said spacer and said spacer engages said fastener, said fastener and said housing being manually movable relative to each other against said force when said longitudinal member is disengaged from said spacer and said member applies said force; and a clamping mechanism that clamps said longitudinal member, said spacer and said housing to said fastener to prevent movement of said fastener relative to said housing, wherein said housing includes a portion deformable to retain said positioning member in said housing.

17. An apparatus as defined in claim 16 wherein said positioning member includes a ring member extending into a groove in said spacer and a groove in said housing.

18. An apparatus as defined in claim 17 wherein said ring member has a gap to permit radial contraction and radial expansion of said ring member.

19. An apparatus as defined in claim 18 wherein said spacer includes axially extending slots that receive a tool for inserting said spacer and said ring member into said housing, said slots intersecting said groove in said spacer to permit engagement of said tool with said ring member to radially contract said spring member into said groove in said spacer.

20. An apparatus as defined in claim 17 wherein said ring member is arched when said ring member is disengaged from said housing and said spacer.

21. An apparatus as defined in claim 16 wherein said force applied by said positioning member to prevent relative movement between said fastener and said housing when said spacer engages said fastener is adjustable.

22. An apparatus as defined in claim 21 wherein said member is positionable in any one of a plurality of axial positions relative to said housing to adjust said force.

23. An apparatus as defined in claim 22 wherein said housing includes a portion engageable with said member to limit the axial position of said member.

24. An apparatus as defined in claim 23 wherein said housing includes a radially extending surface engageable with said member to limit the axial position of said member.

25. An apparatus as defined in claim 24 wherein said member includes a radially extending surface engageable with said radially extending surface on said housing.

26. An apparatus as defined in claim 21 wherein said positioning member includes a retaining portion fixedly connected to said housing.

27. An apparatus as defined in claim 26 wherein said retaining portion is press-fit into said housing.

28. An apparatus as defined in claim 26 wherein said positioning member includes a spring member extending from said retaining portion into engagement with said spacer.

29. An apparatus as defined in claim 28 wherein said spring member is formed as one piece with said retaining portion.

30. An apparatus as defined in claim 28 wherein said spring member includes a leaf spring extending from said retaining portion into engagement with said spacer.

31. An apparatus as defined in claim 21 wherein said positioning member includes a spring member engaging said spacer and further including a retaining member engageable with said spring member and said housing to retain said spring member in said housing.

32. An apparatus as defined in claim 31 wherein said spring member is a Bellville washer.

33. An apparatus as defined in claim 21 wherein said housing includes a tapered surface engageable with said member, said tapered surface extending from a first cylindrical surface of said housing having a diameter larger than a radially outer diameter of said member to a second cylindrical surface of said housing having a diameter smaller than said radially outer diameter of said member.

34. An apparatus comprising:

a fastener having a longitudinal axis and engageable with a bone portion;

a housing having a passage with a first transverse dimension, said fastener extending through an opening in said housing into said passage and being movable relative to said housing, said longitudinal axis of said fastener being positionable in any one of a plurality of angular positions relative to said longitudinal axis of said passage;

a spacer received in said passage of said housing and engageable with said fastener, the spacer having a radial surface having a transverse dimension smaller than said first transverse dimension of said passage in the housing;

a retaining structure having a second transverse dimension greater than the first transverse dimension so that the retaining structure can be press-fit into the passage, the retaining structure and the passage being deformable relative to one another to adjust the distance between said retaining structure and the radial surface of the spacer; and a ring-shaped positioning member positioned between the retaining structure and the spacer, said positioning member configured to apply an adjustable force to the radial surface of the spacer to prevent relative movement between said fastener and said housing when said spacer engages said fastener, the force being adjustable by the distance between the retaining structure and the radial surface;

said fastener and said housing being manually movable relative to each other against said force when said member applies said force.

35. An apparatus as defined in claim 34, wherein the retaining structure and the positioning member are integral.

36. An apparatus comprising:

a fastener having a longitudinal axis and engageable with a bone portion;

a housing having a passage with a first transverse dimension, said fastener extending through an opening in said housing into said passage and being movable relative to said housing, said longitudinal axis of said fastener being positionable in any one of a plurality of angular positions relative to said longitudinal axis of said passage;

a spacer received in said passage of said housing and engageable with said fastener, the spacer having an upper end, a lower end, and a transverse dimension smaller than said first transverse dimension of said passage in the housing;

a retaining structure having a second transverse dimension greater than the first transverse dimension so that the retaining structure can be press-fit into the passage, the retaining structure and the passage being deformable relative to one another to adjust the distance between said retaining structure and the spacer; and a positioning member positioned between the retaining structure and the spacer, said positioning member configured to apply an adjustable force to the spacer to prevent relative movement between said fastener and said housing when said spacer engages said fastener, the force being adjustable by the distance between the retaining structure and the spacer;

said fastener and said housing being manually movable relative to each other against said force when said member applies said force;

wherein the positioning member is a ring-shaped positioning member.

* * * * *

UNITED STATES PATENT AND TRADEMARK OFFICE
CERTIFICATE OF CORRECTION

PATENT NO.         : 7,144,396 B2                                           Page 1 of 1
APPLICATION NO. : 10/483605
DATED              : December 5, 2006
INVENTOR(S)        : Alan E. Shluzas It is certified that error appears in the above-identified patent and that said Letters Patent is hereby corrected as shown below:

Column 26, line 25, after "about" delete "100" and insert --10°--.

Signed and Sealed this

Twenty-seventh Day of March, 2007

JON W. DUDAS
*Director of the United States Patent and Trademark Office*

UNITED STATES PATENT AND TRADEMARK OFFICE
CERTIFICATE OF CORRECTION

PATENT NO. : 7,144,396 B2
APPLICATION NO. : 10/483605
DATED : December 5, 2006
INVENTOR(S) : A. Shluzas It is certified that error appears in the above-identified patent and that said Letters Patent is hereby corrected as shown below:

In Column 22, Line 66, please replace "FIGS. 16." with -- FIG. 16 --

In Column 23, Line 19, please replace "(FIG. 2-1)" with -- (FIG. 21) --

In Column 25, Line 56, Claim 6, please replace "fastener," with -- fastener --

Signed and Sealed this

Twelfth Day of June, 2007

JON W. DUDAS
*Director of the United States Patent and Trademark Office*